(12) United States Patent
Nuszen et al.

(10) Patent No.: US 10,013,661 B2
(45) Date of Patent: Jul. 3, 2018

(54) METHOD AND SYSTEM FOR MONITORING PLANT OPERATING CAPACITY

(71) Applicant: Nuvo Ventures, LLC, Houston, TX (US)

(72) Inventors: Jack Nuszen, Houston, TX (US); Thomas Vo, Bellaire, TX (US)

(73) Assignee: Nuvo Ventures, LLC, Houston, TX (US)

( * ) Notice: Subject to any disclaimer, the term of this patent is extended or adjusted under 35 U.S.C. 154(b) by 0 days.

(21) Appl. No.: 14/271,806

(22) Filed: May 7, 2014

(65) Prior Publication Data

US 2014/0324551 A1  Oct. 30, 2014

Related U.S. Application Data

(63) Continuation of application No. 11/988,975, filed as application No. PCT/US2006/032411 on Aug. 17, 2006, now Pat. No. 8,738,424.

(60) Provisional application No. 60/708,990, filed on Aug. 17, 2005.

(51) Int. Cl.
  *G06Q 10/06* (2012.01)
  *G06Q 50/26* (2012.01)
  *G01N 21/3504* (2014.01)
  *G01N 21/85* (2006.01)

(52) U.S. Cl.
  CPC ....... *G06Q 10/063* (2013.01); *G01N 21/3504* (2013.01); *G01N 21/85* (2013.01); *G06Q 10/06313* (2013.01); *G06Q 50/26* (2013.01)

(58) Field of Classification Search
  CPC .................................................. G06Q 10/0637

USPC .......................................................... 705/7.11
See application file for complete search history.

(56) References Cited

U.S. PATENT DOCUMENTS

| | | | | |
|---|---|---|---|---|
| 3,517,190 A | * | 6/1970 | Astheimer | G01N 21/53 250/338.5 |
| 3,716,717 A | * | 2/1973 | Scheidweiler et al. | G08B 7/12 250/554 |
| 3,766,380 A | * | 10/1973 | Menzies | G01N 21/39 250/338.5 |
| 4,160,163 A | * | 7/1979 | Nakauchi | F23N 5/082 250/339.15 |

(Continued)

OTHER PUBLICATIONS

Measurements of infrared and acoustic source distributions in jet plumes (Apr. 2004). NASA.*

(Continued)

*Primary Examiner* — Peter L Ludwig
(74) *Attorney, Agent, or Firm* — Thomas B. Ryan, Patent Agent; Harter Secrest & Emery LLP

(57) ABSTRACT

A monitoring system is disclosed for acquiring output activity, utilization capacity and/or effluent data from an facility on a facility-by-facility and/or an industry-by-industry basis. The system is designed to generate a plant and/or industry output activity database that is updated on a continuous, near continuous, periodic and/or intermittent basis so that subscribers are apprised of changes in plant or overall industry output. A clearing house is also disclosed for distributing the acquired data to subscribers to aid in analyzing, predicting trends, pricing, maintaining, adjusting, minimizing, and/or maximizing individual plant or overall industry output.

14 Claims, 16 Drawing Sheets

(56) References Cited

U.S. PATENT DOCUMENTS

| | | | | |
|---|---|---|---|---|
| 4,160,164 A * | 7/1979 | Nakauchi | F23N 5/082 | |
| | | | 250/339.15 | |
| 4,233,596 A * | 11/1980 | Okamoto | F23N 5/082 | |
| | | | 250/339.15 | |
| 4,390,785 A * | 6/1983 | Faulhaber | G01J 5/60 | |
| | | | 250/330 | |
| 4,555,627 A * | 11/1985 | McRae, Jr. | G01M 3/38 | |
| | | | 250/330 | |
| 4,568,288 A * | 2/1986 | Patteson | G09B 25/02 | |
| | | | 434/219 | |
| 4,622,922 A * | 11/1986 | Miyagaki | F23N 1/022 | |
| | | | 110/185 | |
| 4,795,253 A * | 1/1989 | Sandridge | G01J 3/02 | |
| | | | 250/338.5 | |
| 4,999,498 A * | 3/1991 | Hunt | G01J 3/453 | |
| | | | 250/338.1 | |
| 5,430,293 A * | 7/1995 | Sato | G01M 3/38 | |
| | | | 250/330 | |
| 5,453,618 A * | 9/1995 | Sutton | H04N 3/09 | |
| | | | 250/332 | |
| 5,489,777 A * | 2/1996 | Stedman | G01J 5/602 | |
| | | | 250/330 | |
| 5,583,765 A * | 12/1996 | Kleehammer | G01N 21/3504 | |
| | | | 250/338.5 | |
| 5,599,179 A * | 2/1997 | Lindner | F23N 1/02 | |
| | | | 431/12 | |
| 5,656,813 A * | 8/1997 | Moore | G01N 21/3504 | |
| | | | 250/330 | |
| 5,689,241 A * | 11/1997 | Clarke, Sr. | G08B 21/06 | |
| | | | 340/575 | |
| 5,719,397 A * | 2/1998 | Hallett | G01N 21/3504 | |
| | | | 250/339.13 | |
| 5,726,450 A * | 3/1998 | Peterson | G01N 21/3504 | |
| | | | 250/338.5 | |
| 5,793,889 A * | 8/1998 | Bushman | F41H 11/02 | |
| | | | 244/3.16 | |
| 5,794,549 A * | 8/1998 | Carter | F23M 11/045 | |
| | | | 110/185 | |
| 6,551,094 B2 * | 4/2003 | Fastnacht | F23M 11/045 | |
| | | | 250/554 | |
| 6,622,645 B2 * | 9/2003 | Havlena | F23D 1/00 | |
| | | | 110/188 | |
| 2004/0211900 A1 * | 10/2004 | Johnson | G01N 21/3504 | |
| | | | 250/338.5 | |
| 2005/0207943 A1 * | 9/2005 | Puzey | C12Q 1/04 | |
| | | | 422/82.05 | |

OTHER PUBLICATIONS

Pogorzala, D. (2004). Gas plume species identification by regression analyses. RIT.*

Mesa-Martinez, F. (2007). Measuring performance, power, and temperature from real processors. Univ. of CA.*

Examples: Abstract Ideas, published by USPTO (no date).*

* cited by examiner

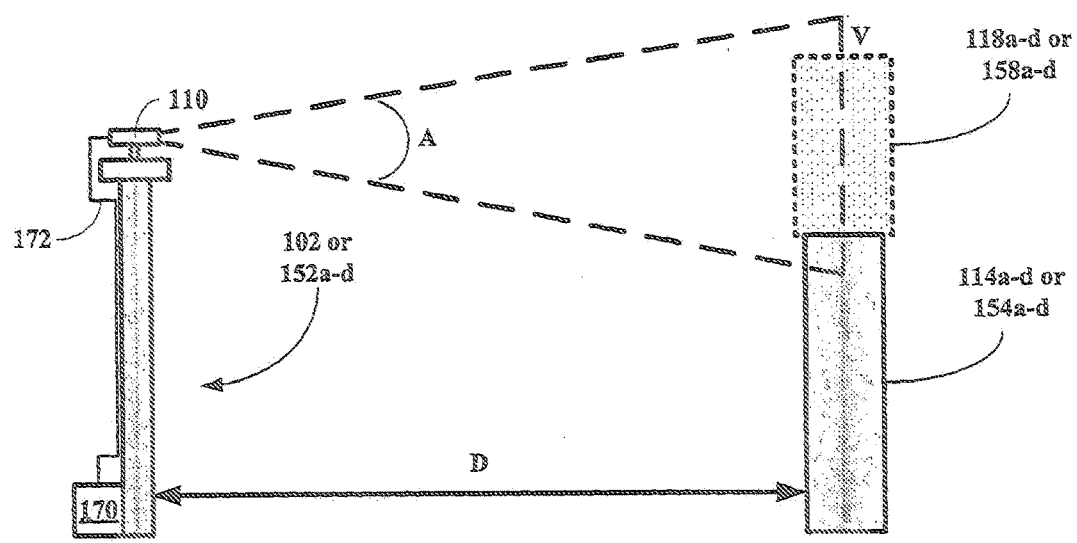
FIG. 1C
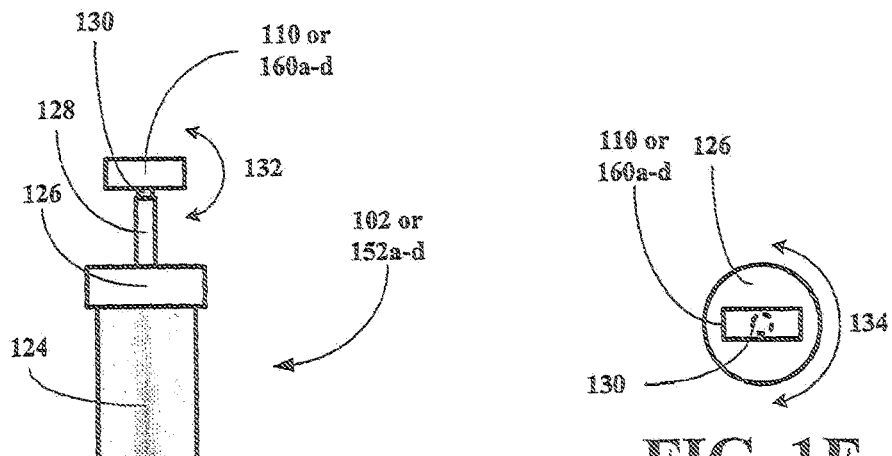
FIG. 1D
FIG. 1E

METHOD AND SYSTEM FOR MONITORING PLANT OPERATING CAPACITY

RELATED APPLICATIONS

This application is a continuation of U.S. patent application Ser. No. 11/988,973 filed Mar. 16, 2009 as a national stage of International Application No. PCT/US2006/032411 filed Aug. 17, 2006, which claims benefit of U.S. Provisional Application No. 60/708,990 filed Aug. 17, 2005.

BACKGROUND OF THE INVENTION

Field of the Invention

The present invention relates to a system and method for monitoring industrial plant activity and to a system and method for using the monitoring data to stabilize plant and industrial productivity, to maximize plant and overall industrial productivity, to track and evaluate plant and industrial productivity, and/or to develop global data dissemination methodologies and/or to develop global industrial responses to natural or man-made industry disruptions.

More particularly, the present invention relates to a system and method for monitoring industrial plant activity, where the method includes imaging plant stacks and/or effluent plumes and relating data derived from the images to an index of plant activity. This invention also relates to a system and method for using the monitoring data to stabilize plant and industrial productivity, to maximize plant and overall industrial productivity, to track and evaluate plant and industrial productivity, and/or to develop global data dissemination methodologies and/or to develop global industrial responses to natural or man-made industry disruptions, where the method includes packaging the plant activity data so that industrial participants and governmental regulatory agencies can change plant and/or industrial output and productivity to adjust, stabilize and/or maximize output of desired industries.

Description of the Related Art

Camera and other detection system designed to image plant effluents and thermal emissions have been used for many years to analyze thermal output and effluent compositions for environmental, operational and emission control. Many of these systems are designed to determine effluent plume composition and effluent plume disbursement. However, such systems have not been used to monitor plant output, down time, cycle time, disruptions, etc. in a real time or near real time so that industry and government can better manage overall output and maintain adequate levels of goods and services and so governments, brokers and analysts can be forecast demand and supply economics.

Thus, there is a need in the art for a system and method for monitoring stack and/or effluent plumes and relating data derived therefrom to a measure of plant productivity and industry productivity and packaging the plant and industry productivity data into a format for instantaneous, periodic or intermittent distribution to broker, analyst, industrial and governmental organizations.

SUMMARY OF THE INVENTION

Systems

The present invention provides a system for monitoring and determining plant output activity or capacity utilization including (1) an imaging subsystem capable of imaging stacks of and/or effluent plumes generated by an industrial facility and/or a unit and/or units thereof to obtain, produce, store and transmit image data. The system also includes (2) an analysis subsystem for converting the image data into plant output activity data or capacity utilization data.

The present invention also provides a system for monitoring and determining plant output activity or capacity utilization including (1) an imaging subsystem capable of imaging stacks of and/or effluent plumes generated by an industrial facility or units thereof to obtain, produce, store and transmit image data. The system also includes (2) a data processing subsystem capable of correcting the image data for existing environmental factors. The system also includes (3) an analysis subsystem for converting the corrected image data into plant output activity or capacity utilization data.

The present invention also provides a system for monitoring and determining plant output activity or capacity utilization including (1) an imaging subsystem capable of imaging stacks of and/or effluent plumes generated by an industrial facility or units thereof to obtain, produce, store and transmit image data. The system also includes (2) an analysis subsystem for converting the image data into plant output activity or capacity utilization data. The system also includes (3) an accumulation subsystem adapted to accumulate the plant output activity or capacity utilization data.

The present invention also provides a system for monitoring and determining plant output activity or capacity utilization including (1) an imaging subsystem capable of imaging stacks of and/or effluent plumes generated by an industrial facility or units thereof to obtain, produce, store and transmit image data. The system also includes (2) an analysis subsystem for converting the image data into plant output activity or capacity utilization data. The system also includes (3) an accumulation subsystem adapted to accumulate the plant output activity or capacity utilization. The system also includes (4) a trend subsystem adapted to determine trends in plant activity or capacity utilization data.

The present invention also provides a system for monitoring and determining plant output activity or capacity utilization including (1) an imaging subsystem capable of imaging stacks of and/or effluent plumes generated by an industrial facility or units thereof to obtain, produce, store and transmit image output activity or capacity utilization data. The system also includes (2) a data processing subsystem capable of correcting the image output data for existing environmental factors. The system also includes (3) an analysis subsystem for converting the corrected image data into plant output activity or capacity utilization data. The system also includes (4) an accumulation subsystem adapted to accumulate the plant output activity or capacity utilization data. The system also includes (5) a trend subsystem adapted to determine trends in plant activity or capacity utilization data.

The present invention also provides a system for monitoring and determining plant output activity or capacity utilization including (1) an imaging subsystem capable of imaging stacks of and/or effluent plumes generated by an industrial facility or units thereof to obtain, produce, store and transmit image output activity or capacity utilization data. The system also includes (2) an analysis subsystem for converting the image data into plant output activity or capacity utilization data. The system also includes (3) an accumulation subsystem adapted to accumulate the plant output activity or capacity utilization data. The system also includes (4) a trend subsystem adapted to determine trends in plant output activity or capacity utilization data. The system also includes (5) a report subsystem designed to report plant and/or industry output capacity, capacity utilization, and overall plant or industrial trends to end users.

The present invention also provides a system for monitoring and determining plant output activity or capacity utilization including (1) an imaging subsystem capable of imaging stacks of and/or effluent plumes generated by an industrial facility or units thereof to obtain, produce, store and transmit image output activity or capacity utilization data. The system also includes (2) a data processing subsystem capable of correcting the image output activity or capacity utilization data for existing environmental factors. The system also includes (3) an analysis subsystem for converting the corrected image output data into plant output capacity data. The system also includes (4) an accumulation subsystem adapted to accumulate the plant output capacity data. The system also includes (5) a trend subsystem adapted to determine trends in plant output data and a report subsystem designed to produce an industry survey of industrial capacity, maximum output, and/or output trends.

The present invention also provides a system for monitoring and determining plant output activity or capacity utilization including (1) an imaging subsystem capable of imaging stacks of and/or effluent plumes generated by an industrial facility or units thereof to obtain, produce, store and transmit image output data. The system also includes (2) an analysis subsystem for converting the image data into plant output capacity data. The system also includes (3) an accumulation subsystem adapted to accumulate the plant output capacity data, a trend subsystem adapted to determine trends in plant output data. The system also includes (4) a report subsystem designed to produce an industry survey of industrial capacity data, maximum output, and output trends. The system also includes (5) an adjustment subsystem designed to adjust individual facility output to adjust and/or maximize overall all industrial output.

The present invention also provides a system for monitoring and determining plant output activity or capacity utilization including (1) an imaging subsystem capable of imaging stacks of and/or effluent plumes generated by an industrial facility or units thereof to obtain, produce, store and transmit image output data. The system also includes (2) a data processing subsystem capable of correcting the image output data for existing environmental factors. The system also includes (3) an analysis subsystem for converting the corrected image data into plant output capacity data. The system also includes (4) an accumulation subsystem adapted to accumulate the plant output capacity data. The system also includes (5) a trend subsystem adapted to determine trends in plant output data. The system also includes (6) a report subsystem designed to produce an industry survey of industrial capacity, maximum output, and/or output trends. The system also includes (7) an adjustment subsystem designed to adjust individual facility output to adjust and/or maximize overall all industrial output.

In all of the above systems, the imaging subsystem can be adapted to image stack plumes to determine temperature and compositional profiles of the plume intermittently, periodically, semi-continuously, or continuously. Thermal and compositional data can either be obtained using a single camera system with different filters that select light characteristic of a given atomic and/or molecular species or using composition specific cameras or sensors in parallel or series. In the case of a single camera system, the imaging system can include a series of filter that are intermittently, periodically or continuously interchanged so that each image type is acquired on an intermittent, periodic or continuous basis. It should be recognized that each data collection for each different filter can be continuously collected or collected over a period of time and if over a period of time, each acquisition period can be the same of different. It should also be recognized that operating in a continuous switching mode does not mean that the collected data for each filter is temporally continuous (clearly when one image is being collected, the other images are not), but that each image type is being collected in a continuous rotation during a given monitoring period. Such a continuous switching mode of operation can be contrasted with a mode where one image type is collected continuously, except for intermittent or periodic collections of the other image types. Thus, the data from the first image type will be temporally much more complete, save for the time required to switch from its filter to a second filter, to collect a data set or image from the second filter and switch back, while the data from the second image type will be intermittent or periodic, with large temporal gaps between the collected data sets or images. Clearly, the data from the first image type will be periodic if the data from the second image type is periodic, but the first data set will have only small temporal data gaps, while the second data set will have large temporal data gaps.

For imaging subsystems having multiple detectors, cameras or sensors, the subsystem can either utilized multiple images (e.g., each camera or sensor can collect its own light) or the subsystem can include one or more beam splitters capable of splitting a single image into a plurality of images. Thus, a single image can be used by all detectors or the number of light collections, images, can be less than or equal to the number of detectors in the imaging subsystem. It should be recognized that the detectors, cameras or sensors convert incident light in an electronic signal that is capable of being analyzed. Generally, the initial electronic signal is an analog signal that is converted into a digital system prior to analyzing the data.

Methods

The present invention provides a method for monitoring and determining plant output activity or capacity utilization including the step of (1) imaging or acquiring image data of stacks of and/or effluent plumes generated by an industrial facility and/or a unit and/or units thereof. Once the image data has been acquired, the method also includes the step (2) analyzing or converting the image data into plant output activity or capacity utilization data.

The present invention also provides a method for monitoring and determining plant output activity or capacity utilization including the step of (1) imaging or acquiring image data of stacks of and/or effluent plumes generated by an industrial facility and/or a unit and/or units thereof. Once the image data has been acquired, the method also includes the step (2) processing the image data to correct the image data for existing environmental factors. After image correction, the method also includes the step (3) analyzing or converting the corrected image data into plant output activity or capacity utilization data.

The present invention also provides a method for monitoring and determining plant output activity or capacity utilization including the step of (1) imaging or acquiring image data of stacks and/or effluent plumes generated by an industrial facility or units thereof. Once the image data has been acquired, the method also includes the step (2) analyzing or converting the image data into plant output activity or capacity utilization data. After data conversion, the method also includes the step of (3) accumulating the plant output activity or capacity utilization data. After data accumulation, the method also includes the step of (4) generating data trends derived from the plant output activity or capacity utilization data.

The present invention also provides a method for monitoring and determining plant output activity or capacity utilization including the step of (1) imaging or acquiring image data of stacks and/or effluent plumes generated by an industrial facility or units thereof. Once the image data has been acquired, the method also includes the step (2) correcting the image data for existing environmental factors. After image data correction, the method also includes the step (3) converting the corrected image data into plant output activity or capacity utilization data. After data conversion the method also includes the step (4) accumulating the plant output activity or capacity utilization data over time. After data accumulation, the method also includes the step (5) generating trends in plant output activity or capacity utilization data.

The present invention also provides a method for monitoring and determining plant output activity or capacity utilization including the step of (1) imaging or acquiring image data of stacks and/or effluent plumes generated by an industrial facility or units thereof. Once the image data has been acquired, the method also includes the step (2) converting the image data into plant output activity or capacity utilization data. After data conversion, the method also includes the step (3) accumulating the plant output activity and capacity utilization data. After data accumulation, the method also includes the step (4) generating trends in plant output activity or capacity utilization data and (5) generating reports derived from the plant output activity or capacity utilization and generated trends for end users.

The present invention also provides a method for monitoring and determining plant output activity or capacity utilization including the step of (1) imaging or acquiring image data of stacks and/or effluent plumes generated by an industrial facility or units thereof. Once the image data has been acquired, the method also includes the step (2) correcting the image data for existing environmental factors. After data correction, the method also includes the step (3) converting the corrected image data into plant output activity or capacity utilization data. After data conversion, the method also includes the step (4) accumulating the plant output activity or capacity utilization data over time. After data accumulation, the method also includes the step (5) generating trends in plant output activity and capacity utilization data and (6) generating reports derived from the plant output activity or capacity utilization and generated trends for end users.

The present invention also provides a method for monitoring and determining plant output activity or capacity utilization including the step of (1) imaging or acquiring image data of stacks and/or effluent plumes generated by an industrial facility or units thereof. Once the image data has been acquired, the method also includes the step (2) converting the image data into plant output activity or capacity utilization data. After data conversion, the method also includes the step (3) accumulating the plant output activity or capacity utilization data over time. After data accumulation, the method also includes the step (4) generating trends in plant output activity or capacity utilization data and (5) generating reports derived from the plant output activity or capacity utilization and generated trends for end users. The method can also include the step of (6) adjusting individual facility output to adjust and/or maximize overall all industrial output or any part thereof.

The present invention also provides a method for monitoring and determining plant output activity or capacity utilization including the step of (1) imaging or acquiring image data of stacks and/or effluent plumes generated by an industrial facility or units thereof. Once the image data has been acquired, the method also includes the step (2) correcting the image output data for existing environmental factors. After data correction, the method also includes the step (3) converting the corrected image data into plant output activity or capacity utilization data. After data conversion, the method also includes the step (4) accumulating the plant output activity or capacity utilization data over time. After data accumulation, the method also includes the step (5) generating trends in the plant output activity or capacity utilization data and (6) generating reports derived from the plant output activity or capacity utilization and generated trends for end users The method can also include the step of (7) adjusting individual facility output to adjust and/or maximize overall all industrial output or any part thereof.

BRIEF DESCRIPTION OF THE DRAWINGS

The invention can be better understood with reference to the following detailed description together with the appended illustrative drawings in which like elements are numbered the same.

FIG. 1C depicts a side view of a system of either FIG. 1A or FIG. 1B.

FIGS. 1D-E depict two views of another embodiment of mount assembly of this invention.

DETAILED DESCRIPTION OF THE INVENTION

Figure 1A:
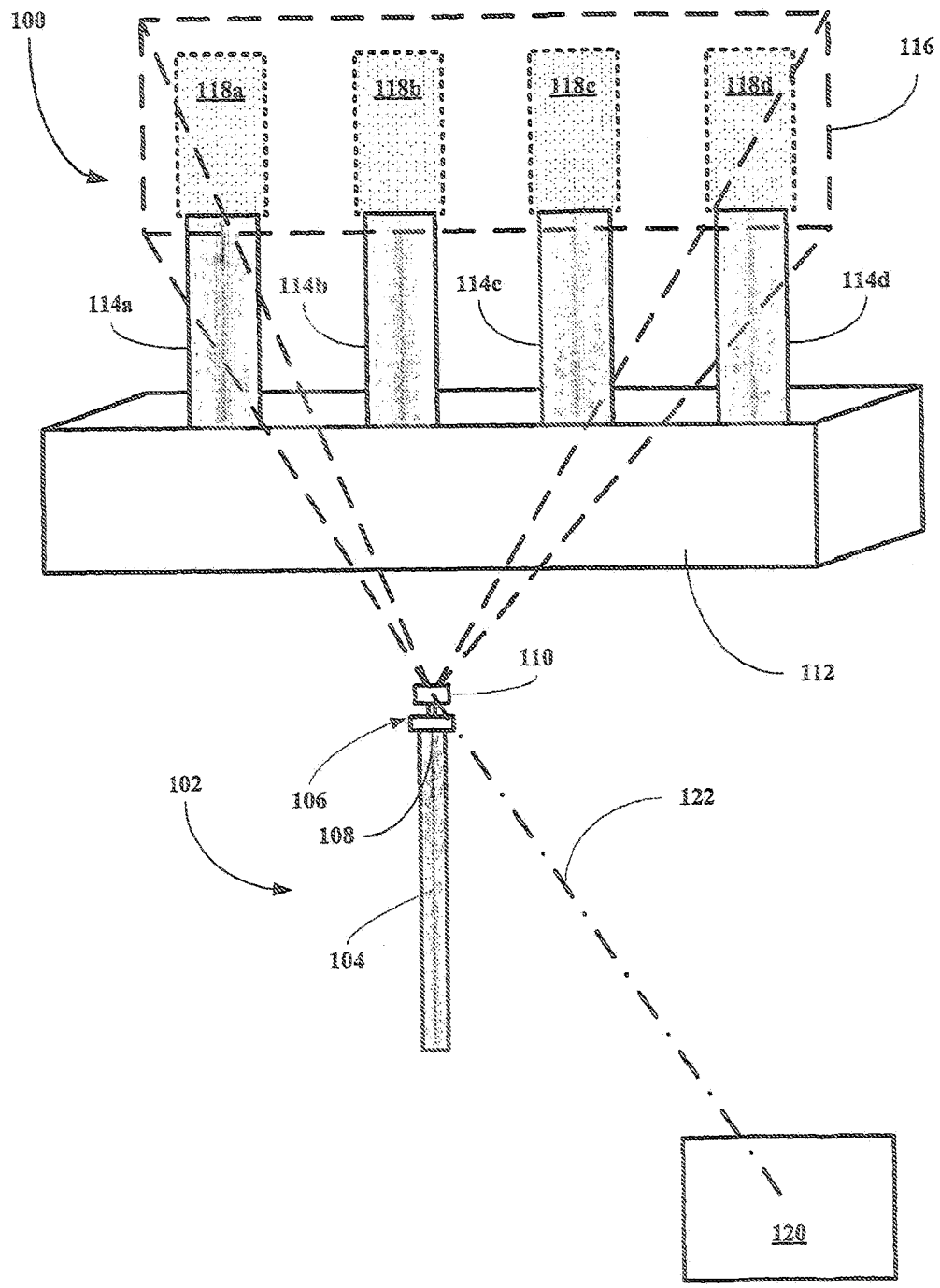
FIG. 1A depicts a block diagram of an embodiment of a plant monitoring system of this invention.

The inventors have found that a system and method can be constructed that uses IR cameras to determine intermittent, periodic, near instantaneous, and/or instantaneous plant capacities of plants of a desired industry. The system and method are designed to utilize data obtained from an IR camera imaging exhaust plumes from exhaust outputs such as stacks outputs. These images are designed to be obtained on an intermittent, periodic, near instantaneous, and/or instantaneous basis and plume size data are then related to a plant activity. The activity data is then used to project overall unit, plant, regional, national, or industrial output to allow for intermittent, periodic, near instantaneous, and/or instantaneous adjustments to overall industrial output so that industrial output across the spectrum can be evened out and/or maximized. The system and method is designed to accumulate data for a sufficient time to determine a base line for determining a particular plant's activity profile so that plume image data can be directly related to plant output within a given confidence level. The system is also designed to provide end users to access unit, plant, regional, industry wide, etc. data on output activity, capacity utilization, emissions, effluent volumes, etc. for forecasting purposes, supply and demand analyses and other industrial indicators. All of the data analyses performed for end users is subject to pricing for revenue generation purposes.

The present invention relates broadly to a system for monitoring and determining plant output capacity including an imaging subsystem capable of imaging effluent plumes generated by an industrial facility or units thereof and producing image output data and an analysis subsystem for converting the image data into plant output capacity data.

The present invention provides. a method for monitoring and determining plant output capacity including an imaging subsystem capable of imaging effluent plumes generated by an industrial facility or units thereof and producing image output data and an analysis subsystem for converting the image data into plant output capacity data.

In order to monitor plant output activity or capacity utilization, a detection device is adapted to observe and/or monitor one property or a plurality of properties of the plant that can be related to plant output activity or capacity utilization. One such property of a plant that can be monitored at a distance is heat associate with thermal stacks and/or stack exhaust effluent streams. For plants that exhaust gases, the detection device is adapted to image an exhaust stack and/or a plume associated with the exhaust stack. The area/volume of the exhaust plume or the stack as imaged by an imaging apparatus such as an IR camera is captured at a given moment in time, continuously captured, or accumulated for a period of time at regular intervals to establish a plant base line or a mean average value of plant output activity or capacity utilization. In the case continuous imaging apparatuses, continuous images are taken over a short period of time at regular intervals, where the images taken over the short periods of time are accumulated to form a single composite image. If the base line or mean average value does not vary by more than a set amount, then the mean average value is set to a 100 percent value. As monitoring continues, deviations from the 100 percent value will either indicate a reduction in plant output or an increase in plant output. If the increase is maintained for a non-temporary time, a new 100 percent value is established. If the 100 percent value originally collected is consistent over time, then changes in the measured value will represent disruptions in the plant output, generally decreases in plant output. If the system is designed to measure non-nuclear power generation facilities, then the data can be used to predict disruptions in the grid and to adjust individual plant outputs to maintain a given level of overall output, to maximize overall output or to adjust overall output to some desired level. In the case of a nuclear power generation facility, the monitor is designed to monitor output water used in the secondary coolant loop in a nuclear power facility or in the effluent water to monitor water temperature, output and to look for detectable radio-pollutants.

The system is designed to monitor plant activity from a distance. Generally, the distance can be between about 25 m (meters) to about 10 km (kilometers) depending on the type of imaging device being utilized. Preferably, the distance is between about 100 m and about 5 km and particularly between about 100 m and about 1 km.

When the system first starts monitoring a given plant, it will not know whether the plant is operating at full capacity. Thus, the system is designed to accumulate data over a sufficient period to time to ascertain whether a given plant output remains substantially constant over the period of time, where the term substantially constant means that the plant output does not deviated more than about 10% over the period of time. In another preferred embodiment, the plant output does not deviate more than about 5% over the period of time. The in yet another preferred embodiment, the plant output does not deviate more than about 1% over the period of time. The period of time is generally a month, preferably, two weeks and, particularly, one week. Once the output of a plant has been determined, its 100 percent is entered into a database.

Generally, plant output data is acquired periodically over the period of time. The period for data acquisition is generally between the acquisition rate of the imaging device, if not continuous, and about 1 day. In a preferred embodiment, the acquisition rate is between about 1 second and 1 hour. In yet another embodiment, the acquisition rate is between about 1 minute and about 1 hour. In yet another embodiment, the acquisition rate is between about 5 minutes and about 45 minutes. In yet another embodiment, the acquisition rate is between about 10 minutes and about 30 minutes. In yet another embodiment, the acquisition rate is between about 10 minutes and about 20 minutes. In yet another embodiment, the acquisition rate is between about 15. This same data acquisition rate is also used for continued monitoring.

Data is then collected for plants within a given industry to form a database for that industry. Once the database is constructed, monitoring allows the system to detect on an instantaneous, a near instantaneous, periodic or intermittent basis alterations in the output of each plant in the given industry. Upon the detection of a disruption in the overall output of a given industry, information associated with the disruption can be sent to local, state and federal oversight agencies and the data can be distributed to other plants within the given industry of the change in overall capacity so that the other plants can adjust their output to compensate for the disruption.

The present invention also relates to a business method for detecting, tracking, compiling and distributing information on an industry-by-industry basis to permit any given industry to adjust specific plant activities so that an overall industrial output can be maintained, adjusted and/or maximized. The information will, of course, be associated with a fee associated with the monitoring, tracking, compiling and distributing of the acquired data. Thus, the present invention also relates to an industry output clearinghouse, where members of a given industry will subscribe to the clearinghouse and will be given data on a continuous, semi-continuous, periodic and/or intermittent basis concerning overall industrial output, output trends, specific plant output data and/or alters signifying changes in the output of one, some or all plants within the given industry. The clearinghouse data will better allow industrial players to determine overall industrial needs and treads and to better adjust individual plant outputs to maintain, adjust, minimize and/or maximize industrial overall output or activity. The clearinghouse data will also be able to identify quickly changes in a specific plant output such as a plant undergoing a de-bottlenecking operation or other modifications to increase plant output. The clearinghouse will give industry players quick and reliable data for maximizing profits, output and/or expenditures to increase specific plant capacity. The clearinghouse data will also show longer term trends in given industries and be able to identify early regional output disruptions or regions where additional capacity is needed to keep up with demand. The data will also allow industrial players to better positions its output capacity to maximize return on investment and to maximize profits and minimize losses.

Suitable IR cameras include, without limitation, IR cameras manufactured by Honeywell Corporation, Thermoteknix Systems Ltd of Cambridge, England (Visir camera, Miric 500, Miric 11, etc.), Infrared Solutions Inc. of Minneapolis, Minn., USA (IR-160), FLIR Systems, Inc. of North Billerica, Mass., USA (A series infrared camera, Thermovision 2000, Thermovision Ranger II and Sentry, etc.), Diversified Optical Products, Inc. of Salem, N.H., USA (Lanscout 50, 75, 125, Lanscout 60/180, Range Pro 50/250, etc.), Leake Company of Dallas, Tex., USA (Thermal Sentry), Spirit Solutions, Inc., and other similar IR camera systems. Preferably, the cameras employ an infrared array detection system. Infrared array detections systems are available from Raytheon Company of Waltham, Mass., USA, DRS Technologies, Inc., Santa Barbara Research Center, University of California at Santa Barbara, Cal Sensors, Inc. of Santa Rosa, Calif., USA, HGH Systemes Infrarouges ZAC, IGNY, FRANCE, ULIS of Veurey Voroize France, and other manufactures that make IR array detectors. It should be recognized that there are different array technologies. Several of these technologies include Amorphous Silicon (ASi) Focal Plane Array (FPA) and Barium Strontium Titanate (BST) FPA. Currently, the inventors have had their best results with the BST FPA array.

Suitable compositional detectors include, without limitation, any detector that is capable of detecting light characteristic of a given atomic and/or molecular system. Generally, the detectors are optimized for a particular wavelength of light and filters are used to eliminate light not in the detectors spectral sensitive regions. However, a detector can be used with broad and uniform response characteristics, with light restriction occurring by judicious selection of filters designed to pass light of a desired wavelength range, where the range is characteristic of a certain chemical compound of class of chemical compounds that have a similar optical emission spectrum within the range. One of ordinary skill in the art are aware of such filters that are selectively sensitive to hydrocarbon optical (Visible, IR, near IR, microwave, etc.) signatures, nitrogen oxide optical signatures, sulfur oxide optical signatures, water (liquid and/or vapor) optical signatures, carbon oxide optical signatures, etc.

Suitable digital processing units include, without limitation, computers having a processing chip and memory chips manufactured by Intel, Motorola, AMD, Cyrix, Erickson, or mixtures or combinations thereof. The digital processing units include peripheral such as, without limitation, internal and/or external mass storage devices such as disk drives, solid state disk drives, tape drives, memory stick, memory cards, etc., communication hardware and software, printers, scanners, etc.

Single Imaging Subsystem—Plume Imaging

Referring now to FIG. 1A, a preferred embodiment of an IR imaging system of this invention, generally 100, is shown to include an imaging assembly 102. In one embodiment, the imaging assembly 102 includes a pole 104, a mount assembly 106 disposed on a top 108 of the pole 104 and an imaging unit 110 mounted on the mount assembly 106. One of ordinary skill in the art should recognize that the imaging assembly 102 can extend from the ground, from the top of a building, or from any other object that allows the imaging unit 110 to have a clear line of sight image of the target plant or plant stacks that are used to obtain information on plant or plant unit activity and to obtain other information including a monitor of the type of materials being exhausted from the stacks. Of course, if the effluent is a liquid, such as waste water, the imaging unit 110 would be situated to image the effluent. If effluent compositional data are being collected as well as plant or plant unit output capacity data, then the imaging unit may include more than one imaging camera, each having a different filter or the imaging unit is capable of collecting data over a large frequency range and the resulting image data can be mathematically filtered.

The imaging assembly 102 is located a specific distance from a plant 112, which is shown to have four exhaust stacks 114a-d, which are monitored to determine the plant's output at any given time. The imaging unit 110 is positioned so that the imaging unit 110 can acquire an image 116 which includes four active regions 118a-d associated with the four stacks 114a-d, respectively. Of course, if it is determined that the four stacks produce equal plant capacity data (each stack accounts for ¼ of the plant output), then only one active region need be analyzed.

The imaging system 100 also includes a remote processing center 120 in data communication with the imaging unit 110 via a data flow pathway 122. The data communication can be wireless or wired. If wireless, the data communication can line of sight or more preferably the signal can be transmitted via cell phone networks or satellite networks onto a distributed network such as the internet or a secured distributor network.

Multiple Imaging Subsystem—Plume Imaging

Figure 1B:
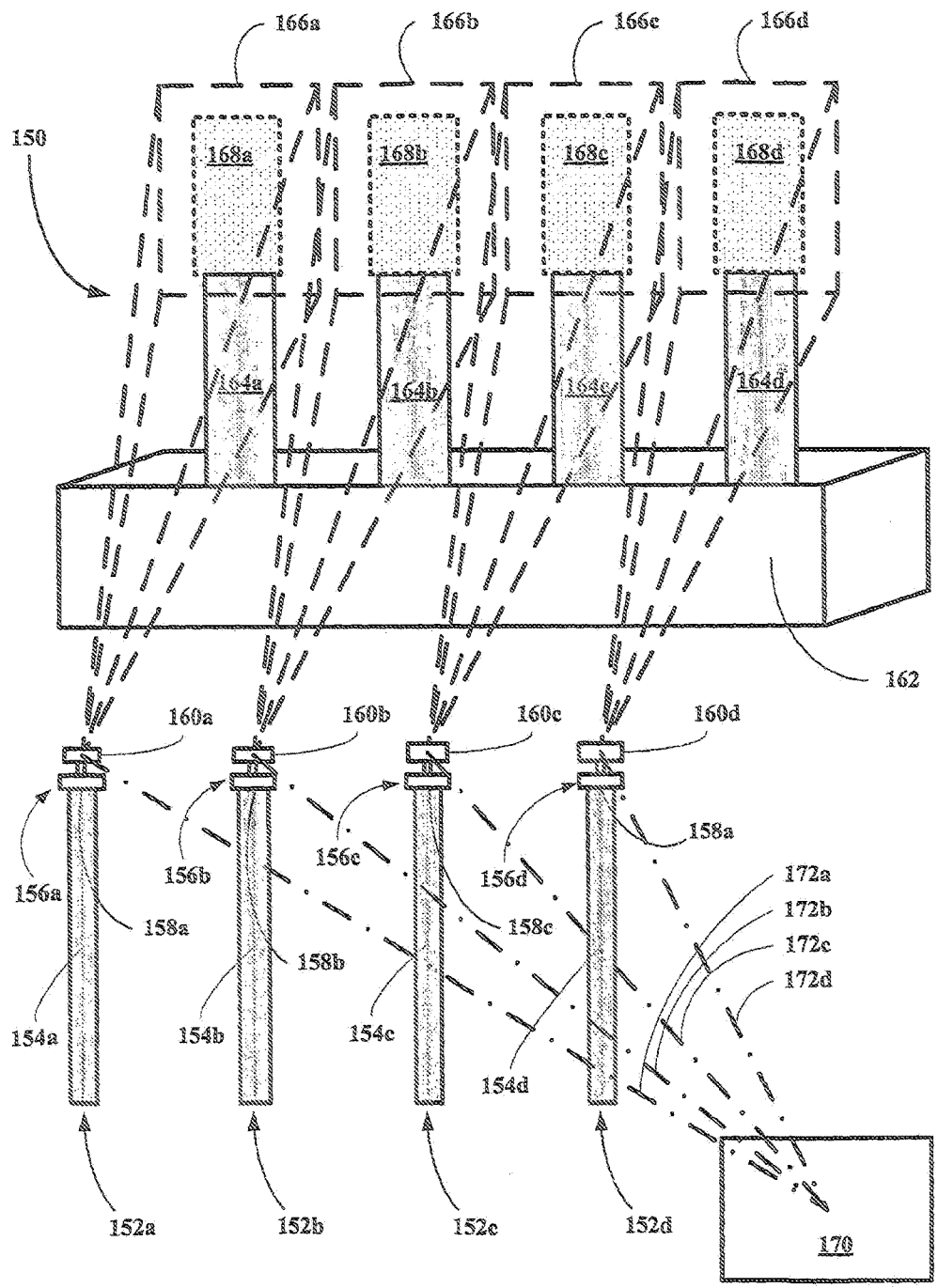
FIG. 1B depicts a block diagram of another preferred embodiment of a plant monitoring system of this invention.

Referring now to FIG. 1B, another preferred embodiment of an IR imaging system of this invention, generally 150, is shown to include four imaging assemblies 152a-d. In one embodiment, each of the imaging assemblies 152a-d includes a pole 154a-d, a mount assembly 156a-d disposed on a top 158a-d of the pole 154a-d and an imaging unit 160a-d mounted on the mount assemblies 156a-d, respectively. One of ordinary skill in the art should recognize that the imaging assemblies 152a-d can extend from the ground, from the top of a building, or from any other object that allow the imaging units 160a-d to have a clear line of sight image of the plant stacks that are used to obtain information on plant or plant unit activity and to obtain other information including a monitor of the type of materials being exhausted from the stacks. Of course, if the effluent is a liquid, such as waste water, the imaging units 160*a-d* would be situated to image the effluent. If effluent compositional data are being collected as well as plant or plant unit output capacity data, then the imaging units may include more than one imaging camera, each having a different filter or the imaging units are capable of collecting data over a large frequency range and the resulting image data can be mathematically filtered.

Each of the imaging assemblies 152*a-d* is located a specific distance from a plant 162, which is shown to have four exhaust stacks 164*a-d*, so that the assembly 152*a* is focused on the stack 164*a*, the assembly 152*b* is focused on the stack 164*b*, the assembly 152*c* is focused on the stack 164*c*, and the assembly 152*d* is focused on the stack 164*d*. This configuration allows each stack to be separating monitored which can increase the amount and type of information extractable from the images. This configuration is especially useful when the output stacks of interest are incapable of being efficiently imaged from a single location or the distance from the imaging unit prevents ready complete imaging as in FIG. 1A.

Each of the imaging units 160*a-d* is positioned so that each of the imaging unit 160*a-d* can acquire an image 166*a-d* which includes a stack active region 168*a-d*, respectively.

The imaging system 150 also includes a remote processing center 170 in data communication with the imaging units 160*a-d*, via data flow pathways 172*a-d*. The data communication can be wireless or wired. If wireless, the data communication can line of sight or more preferably the signal can be transmitted via cell phone networks or satellite networks onto a distributed network such as the internet or a secured distributor network.

Imaging Subsystem Views—Plume Imaging

Referring now to FIG. 1C, a side view of the plant configuration of FIGS. 1A&B is shown. The view show an imaging assembly 102 or 152 and the distance D to the stacks and the resulting vertical image positioning V resulting from a view angle A. The apparatus 100 also includes a processing unit 170 in electrical communication via a communication pathway 172 (which can be a cable supporting wired based data communication or a wireless format supporting wireless data communication) with the imaging unit (camera) 110. The processing unit 170 generally includes computer hardware and software and communication hardware and software need to capture, store, analyze and/or transmit the image data captured by the imaging unit 110 to the central processing center 120.

Referring now to FIGS. 1D-E, a preferred embodiment of the mount assembly 106 or 156*a-d* is shown to include a portion 124 of the pole 104 or 154*a-d*. Mounted on the top 108 or 158*a-d* of the pole 104 or 154*a-d*, respectively, is mount 126 supporting a shaft 128, which is attached to the imaging unit 110 or 160*a-d* via a ball joint 130. The ball joint 130 allows the imaging unit 110 or 160*a-d* to be adjusted up and down 132 as shown in FIG. 1D or side to side 134 as shown in FIG. 1E. Of course, the imaging unit 110 or 160*a-d* can be mounted on the mount 126 by any assembly that permits the imaging unit 110 or 160*a-d* to be adjusted in two orthogonal directions, e.g., up and down and side to side. Moreover, the assembly can be motorized so that the imaging unit can be adjusted remotely. Such remote adjust capability can be used to allow the imaging unit to image specific areas of interest. Furthermore, the imaging unit aperture can be motorized under remote control so that the imaging unit can be controlled to image a specific area and to limit the image being captures. The imaging unit can also be equipped with magnifying lens to further refine the imaged area.

Single Imaging Subsystem—Stack and Plume Imaging

Figure 2A:
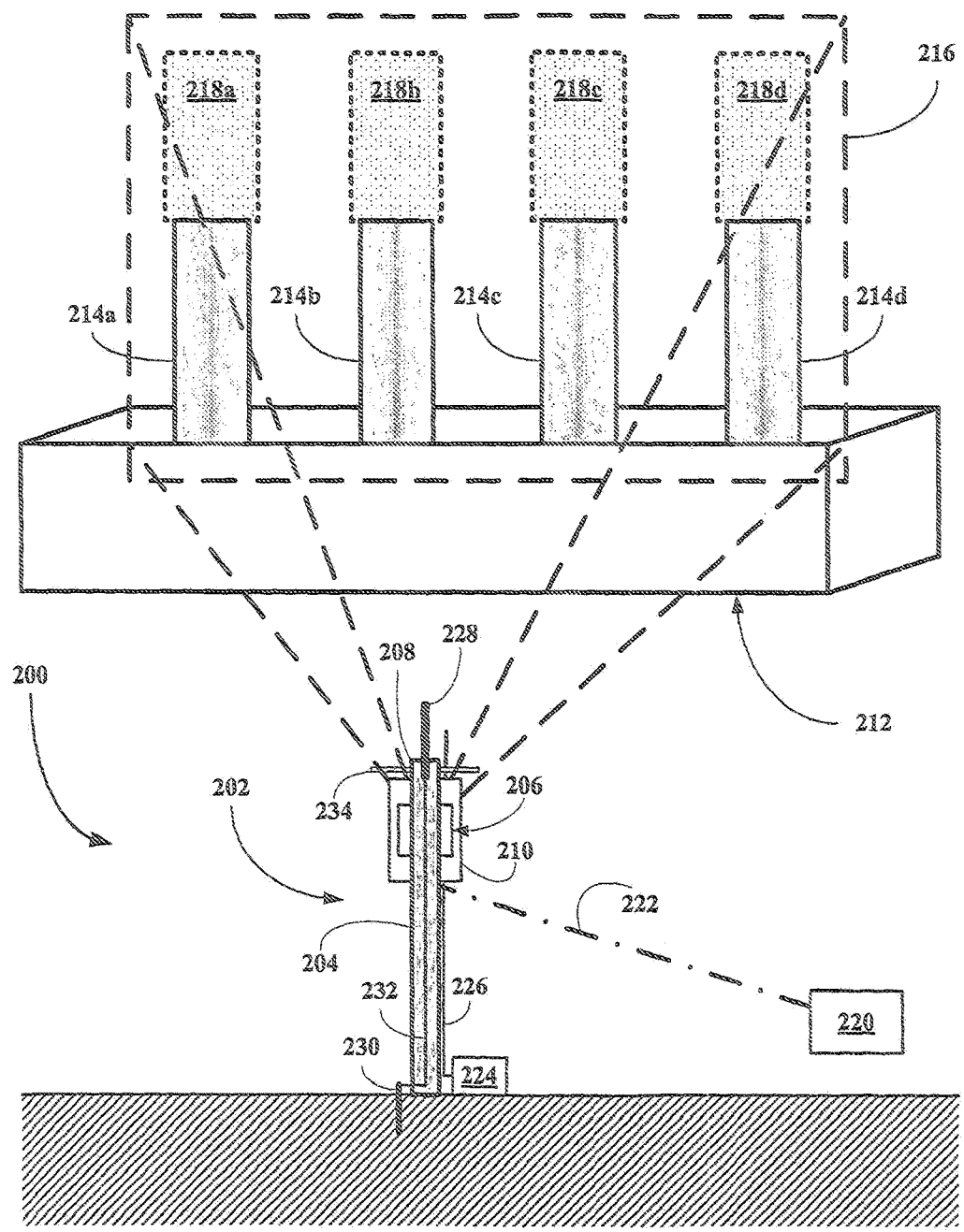
FIG. 2A depicts a block diagram of another embodiment of a plant monitoring system of this invention.

Referring now to FIG. 2A, another embodiment of an IR imaging system of this invention, generally 200, is shown to include an imaging assembly 202. The imaging assembly 202 includes a pole 204, a mount assembly 206 disposed near a top 208 of the pole 204 and an imaging unit 210 mounted on the mount assembly 206. One of ordinary skill in the art should recognize that the imaging assembly 202 can extend from the ground, from the top of a building, or from any other object that allows the imaging unit 210 to have a clear line of sight image of the target plant or plant stacks that are to be used to obtain information on plant or plant unit activity and to obtain other information including monitoring the type of materials being exhausted from the stacks. Of course, if the effluent is a liquid, such as waste water, the imaging unit 210 would be situated to image pipe near its exit and the effluent issued therefrom. If effluent compositional data are being collected as well as plant or plant unit output activity and capacity utilization data, then the imaging unit may include more than one imaging camera and/or detector, each having a different filter or the imaging unit is capable of collecting data over a large frequency range and the resulting image data can be physically or mathematically filtered pre- or post-data acquisition.

The imaging assembly 202 is located a specific distance from a plant 212, which is shown to include four exhaust stacks 214*a-d*, which are monitored to determine the plant's output activity or capacity utilization at any given time or time interval. The imaging unit 210 is positioned so that the imaging unit 210 can acquire an image 216 which includes four the four stacks 214*a-d* and four active regions 218*a-d* associated with the four stacks 214*a-d*, respectively. Of course, if it is determined that the four stack produce equal plant output activity or capacity utilization data (each stack accounting for ¼ of the plant output), then only one stack and/or active region need be analyzed.

The imaging system 200 also includes a remote data storage, processing and analyzing center 220 in data communication with the imaging unit 210 via a data flow pathway 222. The data communication can be wireless or wired. If wireless, the data communication can line of sight or more preferably the signal can be transmitted via cell phone networks or satellite networks onto a distributed network such as the internet or a secured distributor network.

The imaging unit 210 also includes a power conditioning unit 224 connected to a power grid (not shown) and to the imaging unit 210 via a power supply line 226. The imaging unit 210 also includes a lightning rod 228 connected to a ground 230 by a ground wire 232. The assembly 202 also includes a protective top shield 234.

Multiple Imaging Subsystem—Stack and Plume Imaging

Figure 2B:
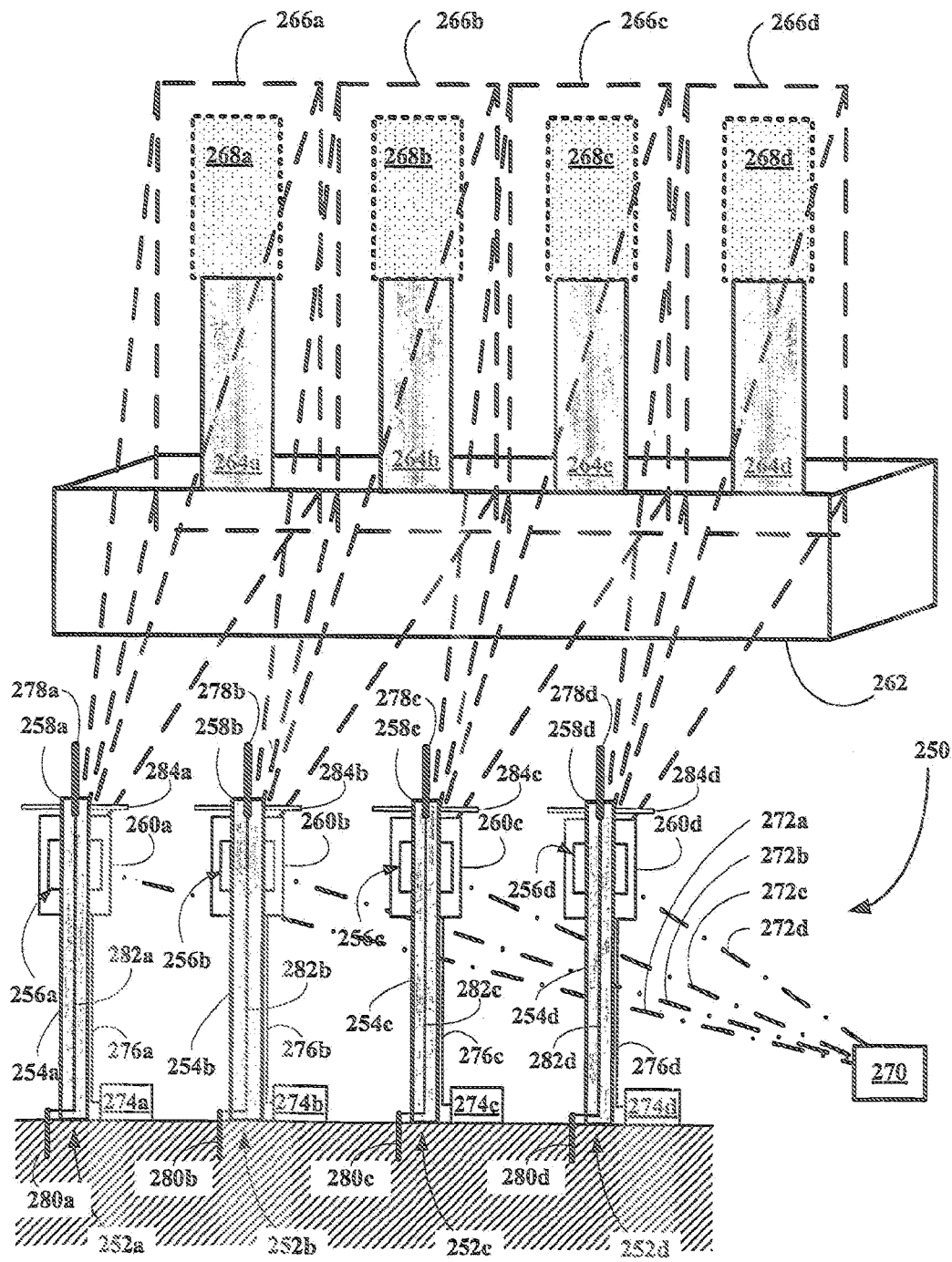
FIG. 2B depicts a block diagram of another preferred embodiment of a plant monitoring system of this invention.

Referring now to FIG. 2B, another embodiment of an IR imaging system of this invention, generally 250, is shown to include four imaging assemblies 252*a-d*. In one embodiment, each of the imaging assemblies 252*a-d* includes a pole 254*a-d*, a mount assembly 256*a-d* disposed on a top 258*a-d* of the pole 254*a-d* and an imaging unit 260*a-d* mounted on the mount assemblies 256*a-d*, respectively. One of ordinary skill in the art should recognize that the imaging assemblies 252*a-d* can extend from the ground, from the top of a building, or from any other object that allow the imaging units 260*a-d* to have a clear line of sight image of the plant stacks that are used to obtain information on plant or plant unit activity and to obtain other information including a monitor of the type of materials being exhausted from the stacks. Of course, if the effluent is a liquid, such as waste water, the imaging units 260a-d would be situated to image the effluent. If effluent compositional data are being collected as well as plant or plant unit output capacity data, then the imaging units may include more than one imaging camera, each having a different filter or the imaging units are capable of collecting data over a large frequency range and the resulting image data can be mathematically filtered.

Each of the imaging assemblies 252a-d is located a specific distance from a plant 262, which is shown to have four exhaust stacks 264a-d, so that the assembly 252a is focused on the stack 264a, the assembly 252b is focused on the stack 264b, the assembly 252c is focused on the stack 264c, and the assembly 252d is focused on the stack 264d. This configuration allows each stack to be separating monitored which can increase the amount and type of information extractable from the images. This configuration is especially useful when the output stacks of interest are incapable of being efficiently imaged from a single location or the distance from the imaging unit prevents ready complete imaging as in FIG. 2A.

Each of the imaging units 260a-d is positioned so that each of the imaging unit 260a-d can acquire an image 266a-d which includes the stacks 264a-d and stack active regions 268a-d, respectively.

The imaging system 250 also includes a remote processing center 270 in data communication with the imaging units 260a-d, via data flow pathways 272a-d. The data communication can be wireless or wired. If wireless, the data communication can line of sight or more preferably the signal can be transmitted via cell phone networks or satellite networks onto a distributed network such as the internet or a secured distributor network.

The imaging units 260a-d also include power conditioning units 274a-d connected to a power grid (not shown) and to the imaging units 260a-d via power supply lines 276a-d. The imaging units 260a-d also include lightning rods 278a-d connected to grounds 280a-d by ground wires 282a-d. The assemblies 252a-d also includes protective top shields 284a-d.

Alternate Single Imaging Subsystem

Figure 3A:
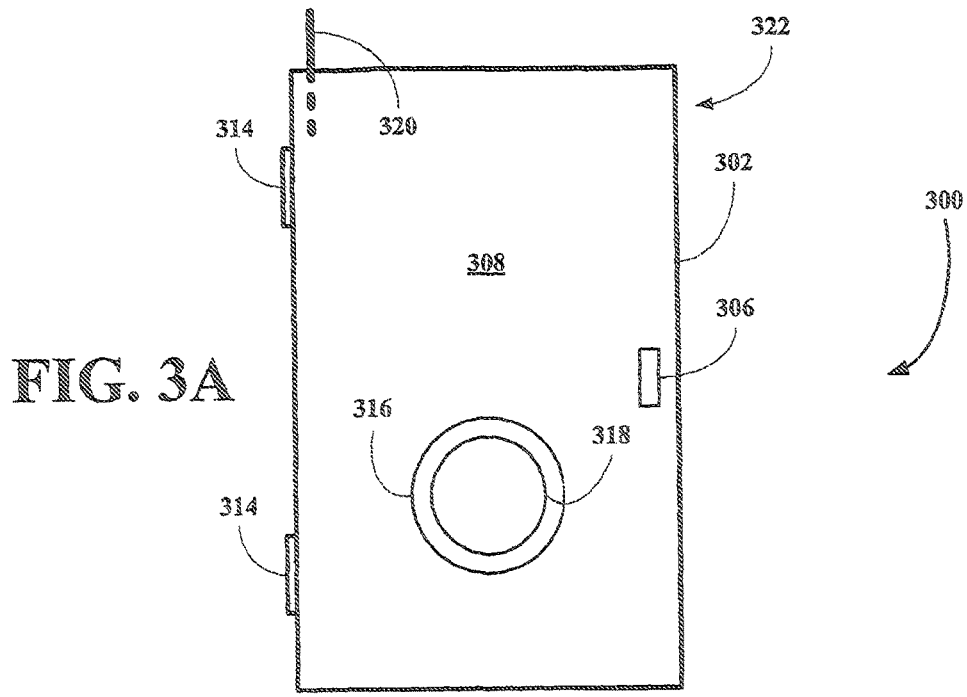
FIGS. 3A&B depict a block diagram of another embodiment of an imaging apparatus of this invention.
Figure 3B:
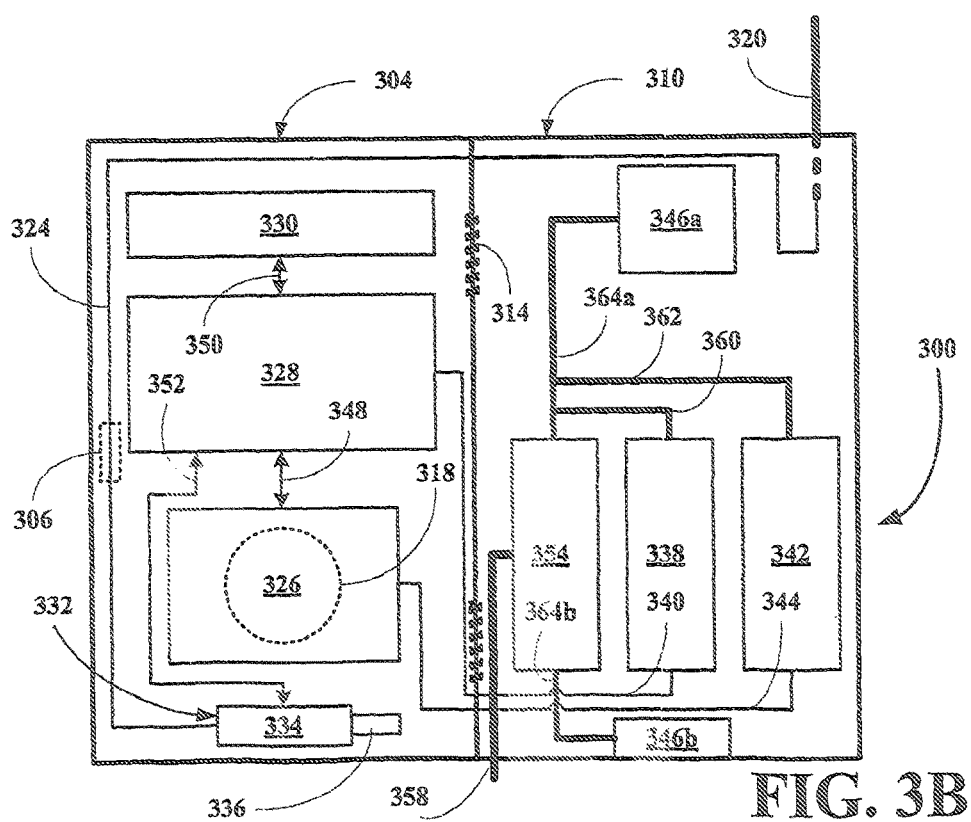
FIG. 3C depicts an imaging apparatus of FIGS. 3A&B mounted on a pole.
FIG. 3D depicts a cross-sectional view of the mount of FIG. 3C.
Figures 3C, 3D:
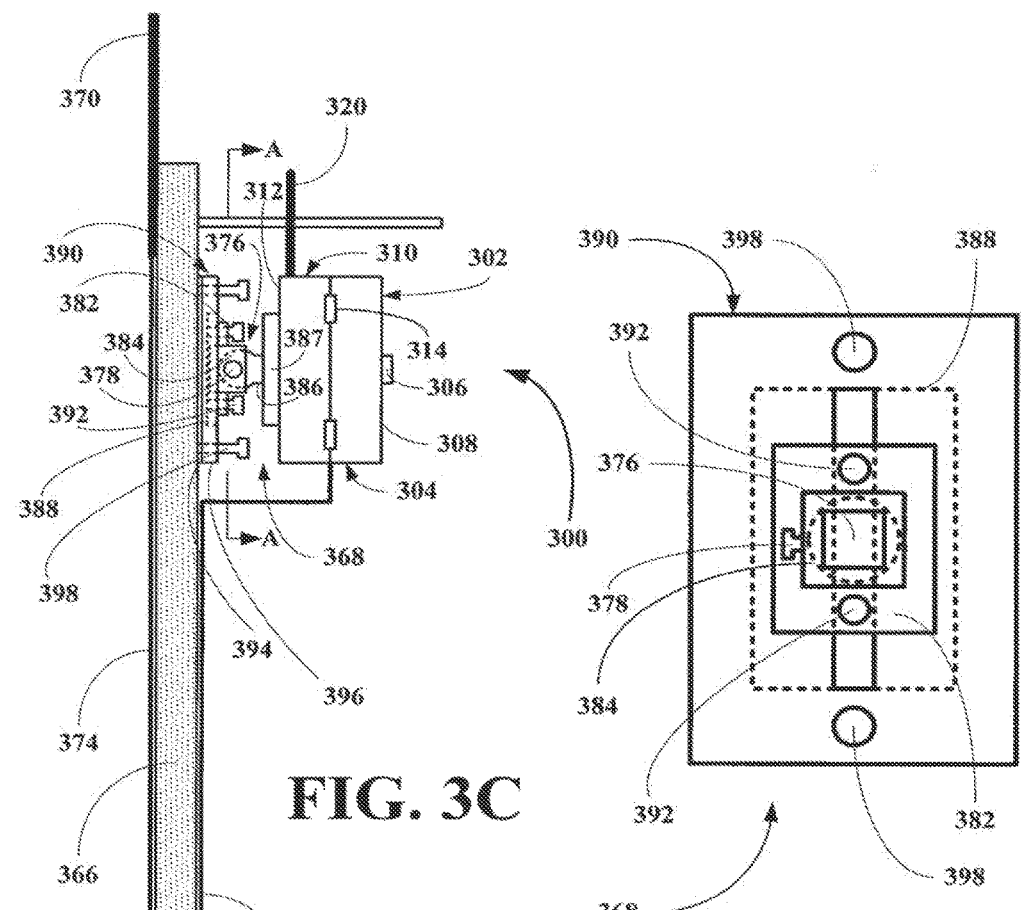

Referring now to FIGS. 3A&B, another embodiment of an imaging apparatus of this invention, generally 300, is shown to include a housing 302 having a front half 304 including a handle 306 attached to a front surface 308 thereof and a back half 310 including a back surface 312 adapted to permit the housing 302 to be mounted on a mount as shown in FIG. 3C. The housing 302 also includes a pair of hinges 314 adapted to permit the housing 302 to be opened by pulling on the handle 306. Of course, the handle can and generally will be a locking handle which requires a key for entry. Alternatively, the housing 302 can be equipped with a keyless entry system that is can be activated by a remote control or via commands issued from a central control facility to prevent unauthorized entry into the apparatus 300.

The front surface 308 include an aperture 316 through which light can pass through a camera lens 318. The apparatus 300 also includes an antenna 320 mounted on the surface 308 near its top 322 having a wire 324 leading to communication hardware to be described below.

Once the apparatus 300 is opened as shown in FIG. 3B, the apparatus 300 includes a camera 326 mounted in the front half 304 of the housing 302 so that its lens 308 centered in the aperture 316. The apparatus 300 also includes a digital processing unit (DPU) 328, a video analog to digital converter 330, and a communication device 332 such as a PIMCIA slot 334 with a mobile access card 336.

The DPU 328 is powered by a DPU power supply 338 mounted in the back half 310 of the housing 302 via a DPU power cable 340; while the camera 326 is powered by a camera power supply 342 mounted in the back half 310 of the housing 302 via a camera power cable 344 The apparatus 300 also includes two fans 346a&b mounted in the back half 310 of the housing 302.

The DPU 328 is in two-way communication with the camera 326 via a first electronic connection 348, with the converter 330 via a second electronic connection 350 and with the communication device 332 via a first electronic connection 352. The communication device 332 is also connected to the antenna 320 via the wire 324, where the antenna is adapted to permit robust communication between the apparatus 300 and a remote command and control site located remote from the site of installation of the apparatus 300 via satellite, microwave or other broadband or narrow band technology capable of transmitted data from the apparatus 300 to a remote site. Alternatively, could have a cable or fiber optics direct connection between the apparatus 300 and the remote control and command center.

The apparatus 300 also includes a power strip 354 connected to an external power conditioner and uninterrupted power supply 356 via a power in cable 358. The power supply 356 can be an outdoor uninterrupted power supply (UPS) with 400 w output for up to 18 hr, 12-14 hr actual. The DPU power supply 338 derives its power from the strip 354 via a first strip cable 360; the camera power supply 342 derives its power from the strip 354 via a second strip cable 362; and the two fans 346a&b derive their power from the strip 354 via third and fourth strip cables 364a&b.

Referring now to FIG. 3C, the apparatus of FIGS. 3A&B is shown mounted on a pole 366 via a mounting apparatus 368 having two degrees of rotational freedom, up and down adjustability and in and out adjustability. The pole 366 includes a lightning rod 370 connected to a ground 372 via a ground wire 374.

One embodiment of the mounting apparatus 368 includes a rotational ball-pen assembly 376 having a locking screw, set screw or thumb screw 378 is shown in FIG. 3D. The ball-pen assembly 376 includes a ball housing 380 affixed to a up and down translation platform 382 and a ball 384 having a neck 386 affixed to a monitoring apparatus mount 387 affixed to a back surface 312 of the back half 310 of the housing 302. The ball-pen assembly 376 permits the monitoring apparatus 300 to be tilted so that its camera aperture 316 is properly aligned with the stack or other object that the monitoring system 300 is installed to monitor (stacks, refinery units, heat exchange units, chemical reactor units, power plant water outlets, steam generation units, etc.). The translation platform 382 is adapted to translate via a groove 388 in a pole mounting plate assembly 390. The translation platform 382 is held in place by to groove engaging screws 392. The pole mounting plate assembly 390 includes a pole plate 394 affixed to the pole 366 and an adjustable plate 396, which comprises the groove into which the translation platform 382 is mounted. The adjustable plate 396 is adapted to be separated from the pole plate 394 by screws 398, which force the plates 394 and 396 to separate or come together depending on the direction the screws are turned. Other mounting apparatuses can be used as well provided that they at least permit two degrees of rotational freedom so that the camera aperture of the monitoring unit can be properly aligned with the object to be imaged. Up and down and in and out adjustability are optional, but are often found to be beneficial then installing the unit as the mounting apparatus does not have to be very precisely attached to the pool. Of course, the extent of rotation freedom will be limited by the ball-pen assembly and the size and weight of the monitoring unit, the size and weight of the mounting apparatus and other factors all within the design capability of an ordinary artisan in the field of mounting equipment on poles with differing rotational and/or translational degrees of freedom. The types of mounts that can be used are any camera or telescope mount that provides at least two rotational degrees of freedom, where translation and in and out adjustment can be made when the unit is being installed or translational adjustment can simply be an adjustable pole strapping assembly.

Multi-Detector Imaging Subsystem

Figure 4:
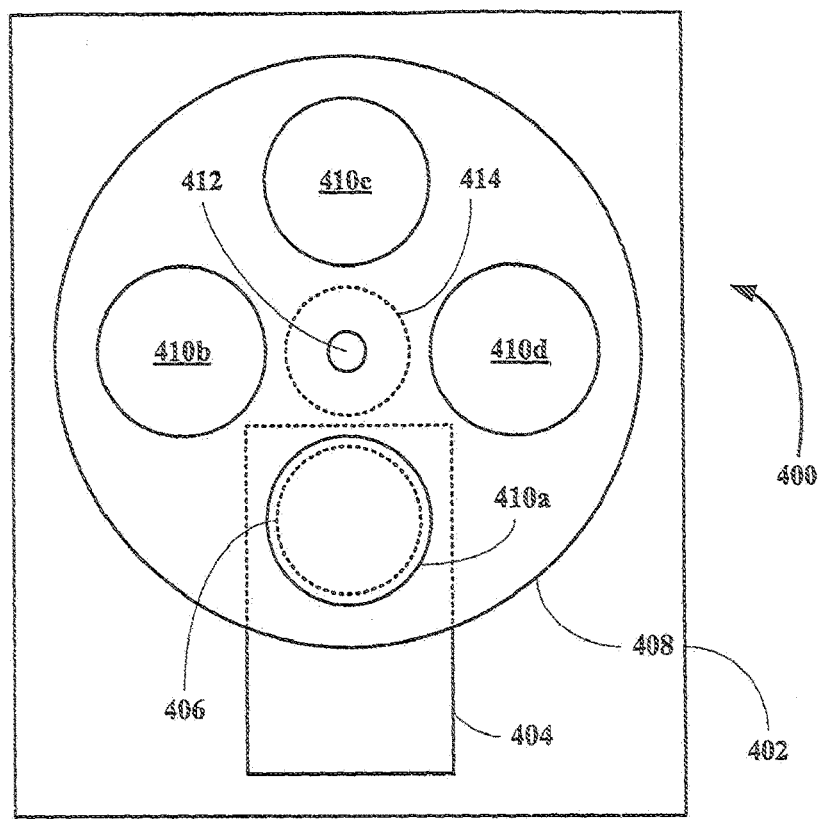
FIG. 4 depicts an embodiment of an imaging apparatus with multiple filters of this invention.

Referring now to FIG. 4, an embodiment of an imaging apparatus with multiple filters of this invention, generally 400, is shown to include a camera housing 402. The camera housing 402 includes a camera 404 having an aperture 406 through which light passes into the camera's interior. The camera housing 402 also includes a four filter carousel 408 including four filters 410a-d. The carousel 408 is mounted on a drive shaft 412 of a motor 414. The motor 414 is adapted to change filters so that the camera can be used to view different properties of the target site such as thermal emission profiles, effluent components ($S_xO_y$, $N_xO_y$, $CO_2$, hydrocarbons, water, etc. or mixtures or combinations thereof, where x is an integer having a value between 1 and 3 and y is an integer having a value between 1 and 8). The motor 414 is adapted to be controlled by the DPU 328 so that the system 300 can collect data on different properties of the site by selectively switching between filters. The apparatus 400 can be used with any of the imaging apparatuses of FIGS. 1-3.

Figure 5:
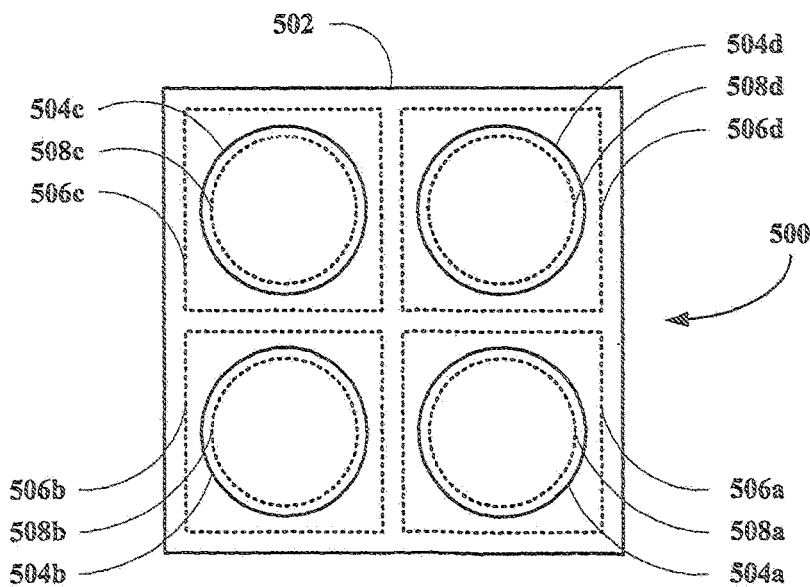
FIG. 5 depicts an embodiment of a multiple camera imaging apparatus of this invention.

Referring now to FIG. 5, an embodiment of a multiple camera imaging apparatus of this invention, generally 500, is shown to include a housing 502. The housing 502 includes four filters 504a-d and four cameras 506a-d having their apertures 508a-d aligned with the filters 504a-d so that light passes through the filters 504a-d through the apertures 508a-d and into the cameras 506a-d. The cameras 506a-d are connected to the DPU or to the converter and then the DPU, where the DPU is designed to capture, process and transmit the captured camera data. The apparatus 500 can be used with any of the imaging apparatuses of FIGS. 1-3.

Figure 6:
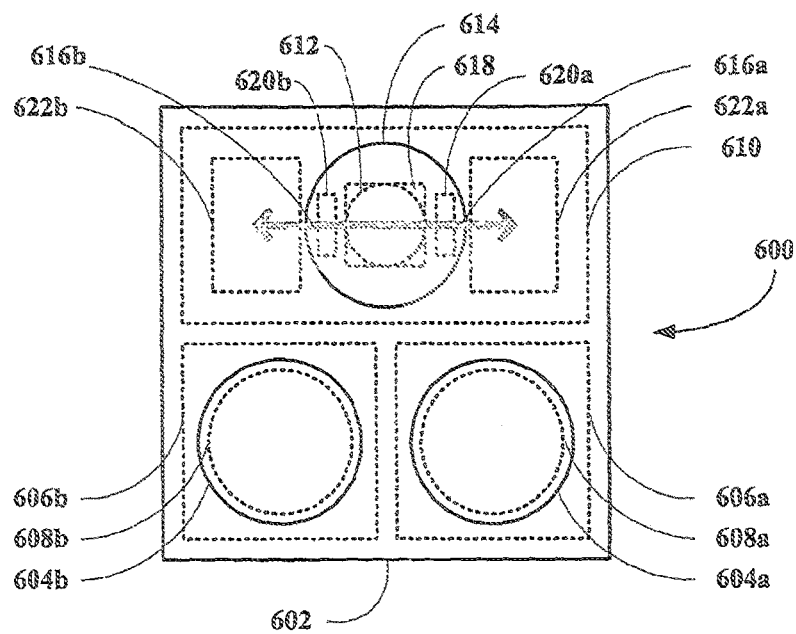
FIG. 6 depicts an embodiment of an imaging apparatus with a beam splitter of this invention.

Referring now to FIG. 6, an embodiment of an imaging apparatus with a beam splitter of this invention, generally 600, is shown to include a housing 602. The housing 602 includes surface mounted two filters 604a-b and two single detector cameras 606a-d having their apertures 608a-b aligned with the filters 604a-b so that light passes through the filters 604a-b through the apertures 608a-b and into the cameras 606a-b. The housing 602 also includes a multi-detector optical detection apparatus or camera 610 having a detector aperture 612 situated within a housing aperture 614 in the housing. Light entering through the detector aperture 612 is split into two beams 616a-b by a beam splitter 618. The first light beam 616a passes through a first detector filter 620a and into a first detector 622a, while the second light beam 616b passes through a second detector filter 620b and into a second detector 622b. The two single channel cameras 606a-b and the multi-channel camera or optical detector 610 are connected to the DPU or to the converter and then the DPU, where the DPU is designed to capture, process and transmit the captured camera data. The apparatus 600 can be used with any of the imaging apparatuses of FIGS. 1-3.

Figure 7:
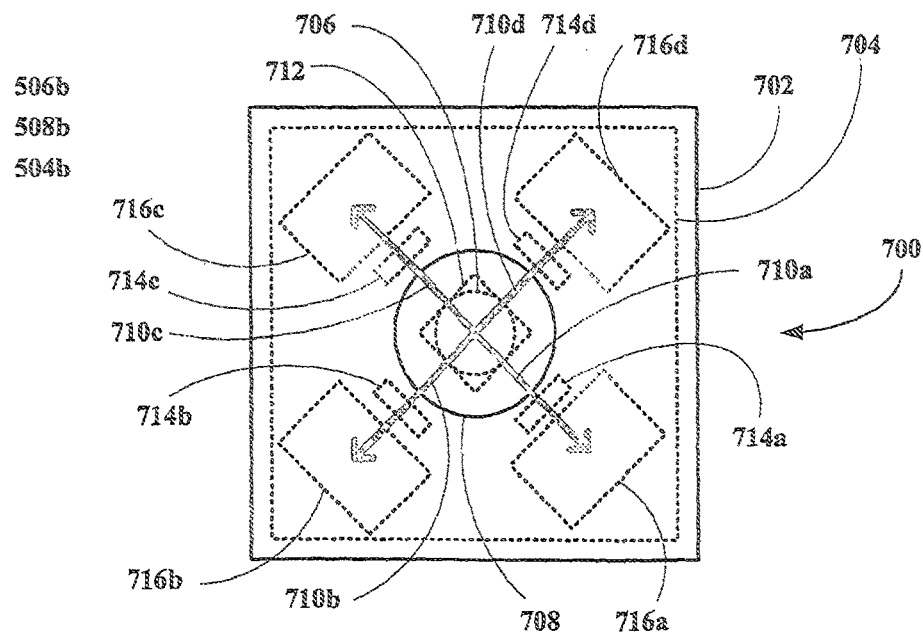
FIG. 7 depicts another embodiment of an imaging apparatus with a compound beam splitter of this invention.

Referring now to FIG. 7, another embodiment of an imaging apparatus with a compound beam splitter of this invention, generally 700, is shown to include a housing 702. The housing 702 includes a multi-detector optical detection apparatus or camera 704 having a detector aperture 706 situated within a housing aperture 708 in the housing. Light entering through the detector aperture 706 is split into four beams 710a-d by a compound beam splitter 712. The first light beam 710a passes through a first detector filter 714a and into a first detector 716a; the second light beam 710b passes through a second detector filter 714b and into a second detector 716b; the third light beam 710c passes through a third detector filter 714c and into a third detector 716c; while the fourth light beam 710d passes through a fourth detector filter 714d and into a fourth detector 716d. The multi-channel camera or optical detector 704 is connected to the DPU or to the converter and then the DPU, where the DPU is designed to capture, process and transmit the captured camera data. The apparatus 700 can be used with any of the imaging apparatuses of FIGS. 1-3.

Multi-Site System

Figure 8:
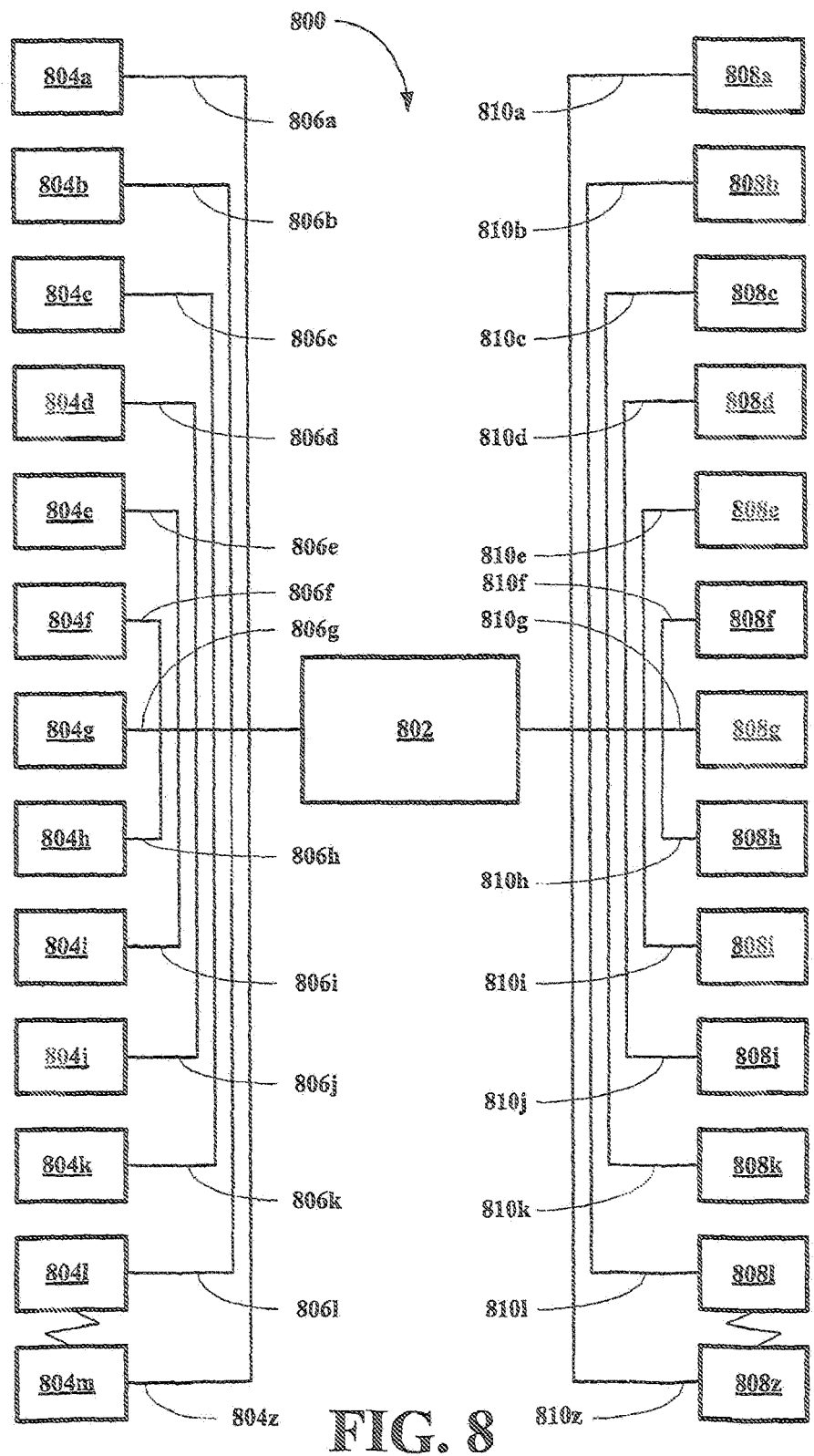
FIG. 8 depict a block diagram of an embodiment of a multi-site system of this invention.

Referring now to FIG. 8, an embodiment of a multi-site system of this invention, generally 800, shown to include a center facility 802 that includes computer hardware and software, communications hardware and software and sufficient servers to support a plurality of site monitoring system 804a-z, where the term a plurality means between 2 and a number limited only by the number of sites amenable to monitoring by this type of a system. Clearly, the upper limit can be many thousands if not many hundreds of thousands of sites. The sites 804a-z are in data communication with the facility 802 via communication pathways 806a-z, which can be wired and/or wireless, but most often will be wireless. Of course, if the data is being transmitted via a commercial or private broadband wireless provider, part of the connection can be wireless and part wired, where the wired part would represent data being received wireless into an intranet (private internet) or open internet like the world wide web.

The data from the monitoring system 804a-z can be raw data, partially processed data or fully processed data. The facility 802 receives this data as is and performs would ever additional data processing required to obtain site specific data-capacity utilization or output activity data, effluent compositional data, effluent production volume data, etc. This process data is then stored on a site specific basis in database on the servers in the facility 802. This accumulated data can then be analyzed on any combination of monitoring systems basis. Thus, if monitoring is occurring at all sites of a particular type such as power plants, then grid integrity reports can be generated to show trends, to identify problems and to predict future supply, demand and pricing.

The system 800 also includes a plurality of end users 808a-z, where the end user plurality can be from 2 to a very large number into the millions of end users. Each end user 808a-z is are in data communication with the facility 802 via communication pathways 810a-z, which can be wired and/or wireless, but most often will be wireless. Of course, if the data is being transmitted via a commercial or private broadband wireless provider, part of the connection can be wireless and part wired, where the wired part would represent data being received wireless into an intranet (private internet) or open internet like the world wide web.

Figure 9:
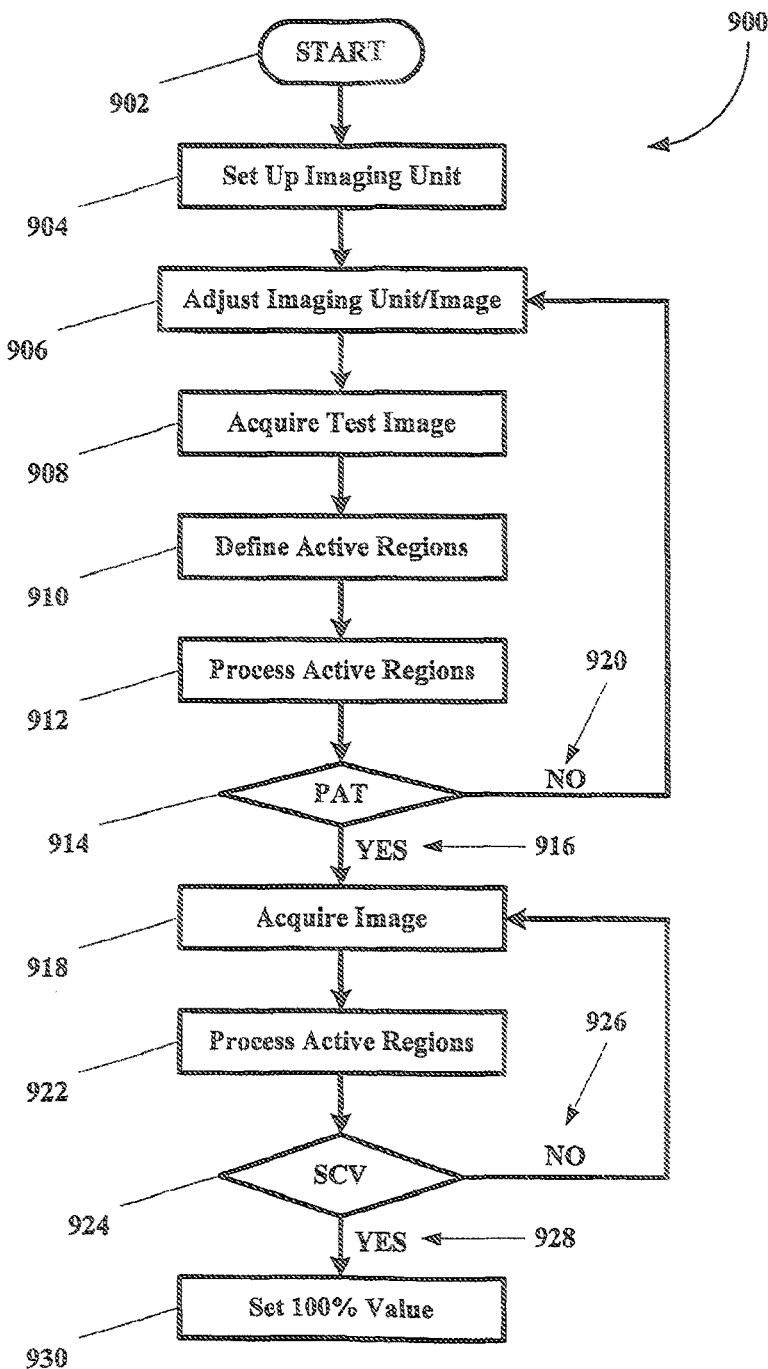
FIG. 9 depicts a conceptual flow chart of a process of initializing, calibrating and establishing a one hundred percent output capacity value for a given plant or plant unit.

Methods for Collecting, Analyzing and Distributing Plant Activity or Utilization Data Referring now to FIG. 9, an embodiment of a process to obtain a one hundred percent plant or plant unit output capacity, generally 900, is shown as a flow chart diagram. The process 900 includes a start step 902, which becomes active after the imaging apparatus has been installed at a desired site. After installation, the imaging unit is set up in a set step 904, which generally involves insuring that all components of the imaging unit are working, that the imaging unit is in communication with the remote processing center and insuring that the imaging unit is functioning properly. Once the imaging unit is set up, the imaging unit is adjusted in an adjustment step 906 by rotating and/or translating the unit on its mount so that the imaging camera or cameras are property aligned with the site to be monitored. A test image is then acquired in an acquisition step 908. The acquired image is then scanned to define active regions within the image in a define active regions step 910. The active regions represent that part of the entire image that will be monitored in all subsequent image acquisitions and can include parts of the operational unit such as a stack, piping, heat exchange units, etc. and/or effluent streams or plumes. Once the active regions are defined, the regions are processes to produce data that can be related to plant activity, unit activity, capacity utilization, effluent production, effluent compositions, etc. in a process active regions step 912. The results are then tested in a conditional pass acquisition test (PAT) step 914. If the imaging unit has been adjusted so that the acquired image maximizes data collections of the target site(s) within the plant, then control is transferred along a YES branch 916 to an acquire image step 918; otherwise control is transferred along a NO branch 920 to the adjustment step 206. This NO loop is continued until the data passes the conditional test 814. The acquired image is then processed to compute a plant or unit output value in a process active regions step 922. The value is then sent to a compare step or self-consistent value (SCV) step 924, where the current value is compared to a previous value or a set of previous values until the values being compared differ by less than a specified percent error. If the difference is greater than the error, then control is transferred along a NO branch 926 to the acquire image step 818 for reacquisition; otherwise control is transferred along a YES branch 928 to a set 100% value step 930. Of course, it should be recognized that the 100% is set when the unit or plant is operating at full capacity. When a unit is initially installed; there is not guarantee that the plant or unit being monitored is actually operating at 100% capacity. However, this routine can be used to set an initial 100% value. If later, the value jumps and remains that the actual 100% valve, then the 100% can be updated. This same updating may occur with the plant or unit undergoes modifications, de-bottlenecking, or any other change that can increase or decrease 100% capacity value.

Figure 10:
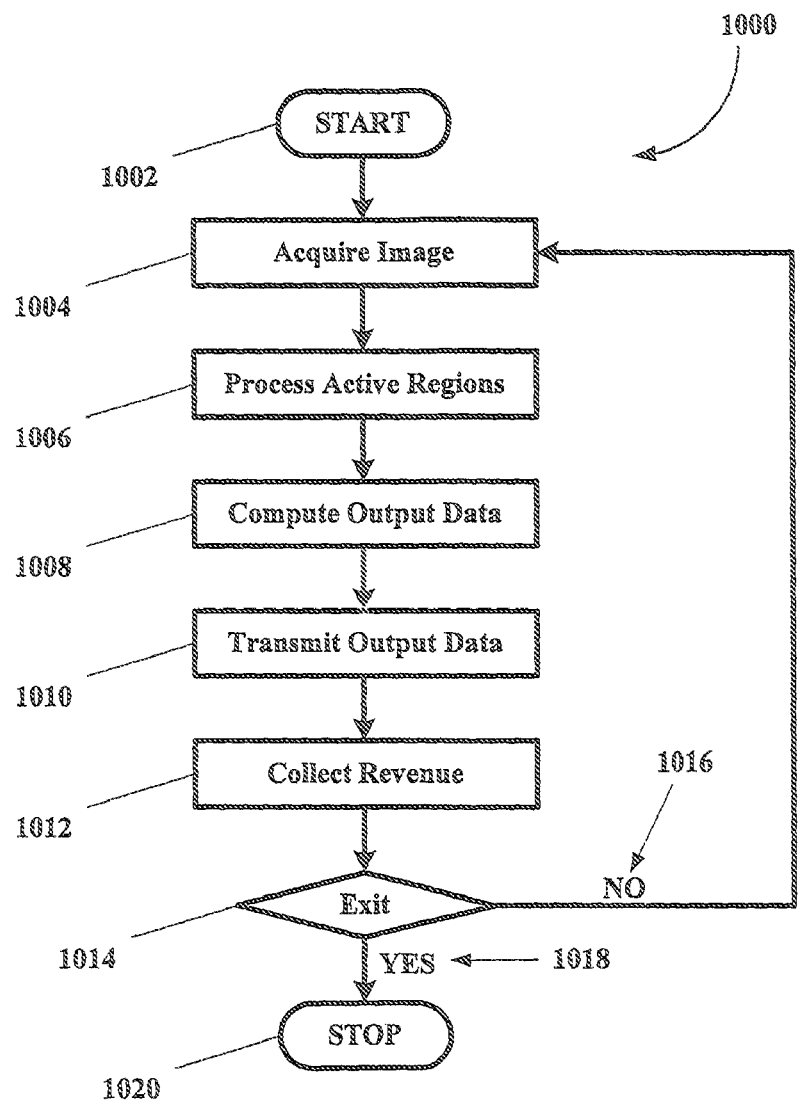
FIG. 10 depicts a conceptual flow chart of a process a plant output monitoring, transmitting and collecting process of this invention.

Referring now to FIG. 10, an embodiment of a process to obtain output capacity data, generally 1000, is shown as a flow chart diagram. The process 1000 begins with a start step 1002. After the routine is started, an image is acquired in an acquire image step 1004. The acquired image is then process to extract data from the active regions within the image in a process step 1006. The active region data is then used to compute output activity, utilization capacity and/or effluent compositional data in a compute step 1008. The output data is then transmitted to a customer in a transmit step 1010 and a revenue is collected as a result of the transfer in a collect step 1012. The process 900 also includes a conditional step 1014, where the process can be stopped by an interruption in collected revenue, discontinuing of an account or by supervisor intervention. If no exit event has occurred, then controlled is transferred along a NO branch 1016 to the acquire image step 304; otherwise control is transferred along a YES branch 1018 to a stop step 1020. Of course, in general, the program will not terminate, but will continue data collection and transmission until no revenue stream is obtained. However, the program could also be continued to accumulate information for periodic compilation and sale. Alternatively, the transmit step 910 can simply be a posting of the results to secure website or a secure server and the end user would simply logon into an account on the website or server and obtain the posted data.

Figure 11:
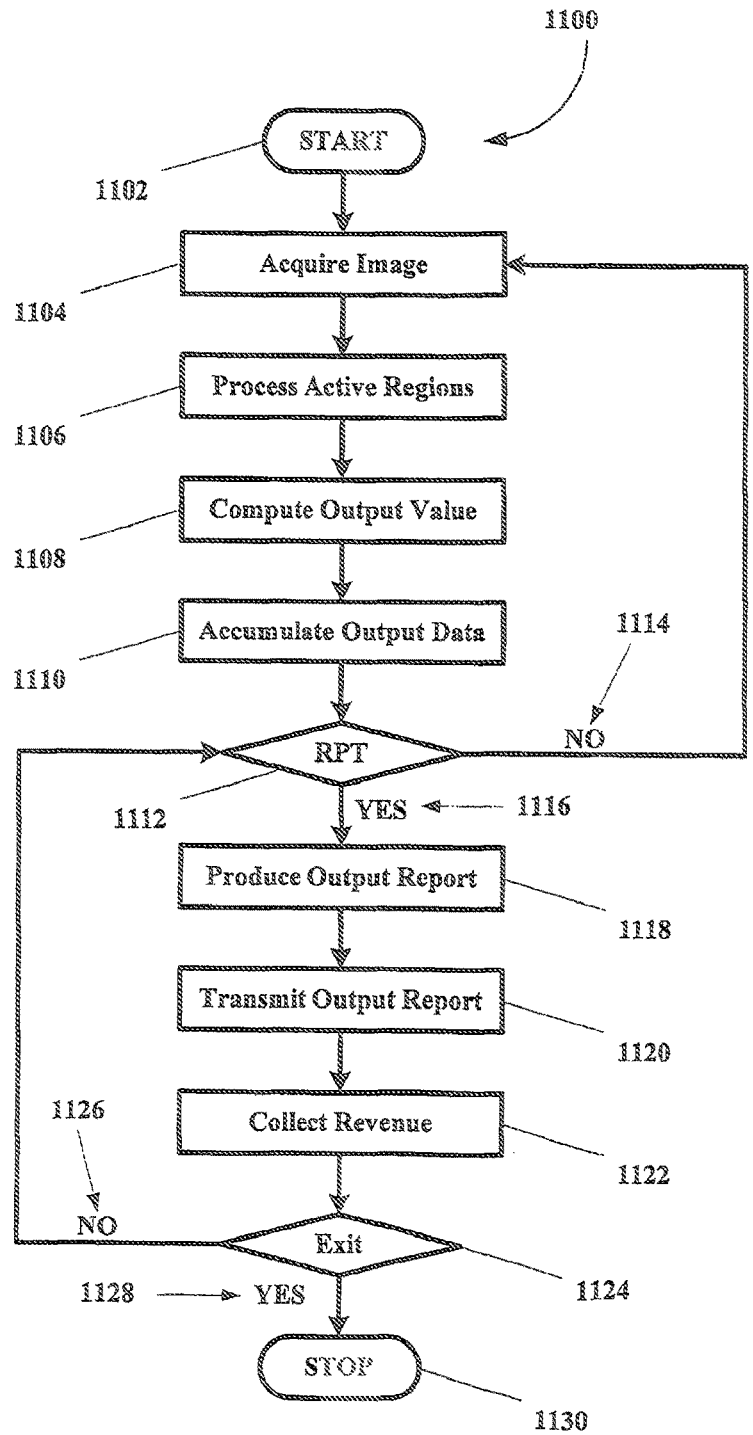
FIG. 11 depicts a conceptual flow chart of another process a plant output monitoring, transmitting and collecting process of this invention.

Referring now to FIG. 11, another embodiment of a process to obtain output capacity data, generally 1100, is shown as a flow chart diagram. The process 1100 begins with a start step 1102. After the routine is started, an image is acquired in an acquire image step 1104. The acquired image is then process to extract data from the active regions within the image in a process step 1106. The active region data is then used to compute output activity, utilization capacity and/or effluent compositional data in a compute step 1108. The data is then accumulated for a period of time, either set, variable or interruption triggered in an accumulate step 1110. Control is then transferred to a report period test (RPT) step 1112. If the period limit or trigger has not occurred, then control is transferred along a NO branch 1114 to the acquire image step 404; otherwise control is transferred along a YES branch 1116 to a product output report step 1118. Once the accumulated output report is produced, the report is transmitted to a customer in a transmit step 1120 and revenue is collected in a collect step 1122. The process 400 also includes a conditional step 1124, where the process can be stopped by an interruption in collected revenue, discontinuing of an account or by supervisor intervention. If no exit event has occurred, then controlled is transferred along a NO branch 1126 to the acquire image step 304; otherwise control is transferred along a YES branch 1128 to a stop step 1130. Of course, in general, the program will not terminate, but will continue data collection and transmission until no revenue stream is obtained. However, the program could also be continued to accumulate information for periodic compilation and sale. Alternatively, the transmit step 1020 can simply be a posting of the results to secure website or a secure server and the end user would simply logon into an account on the website or server and obtain the posted data.

Figure 12A:
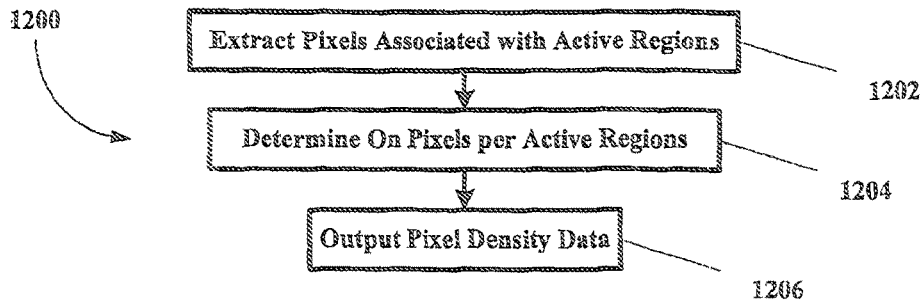
FIGS. 12A-C depict three conceptual flow charts of three subprocesses for processing an acquired image to obtain pixel density data.
Figure 12B:
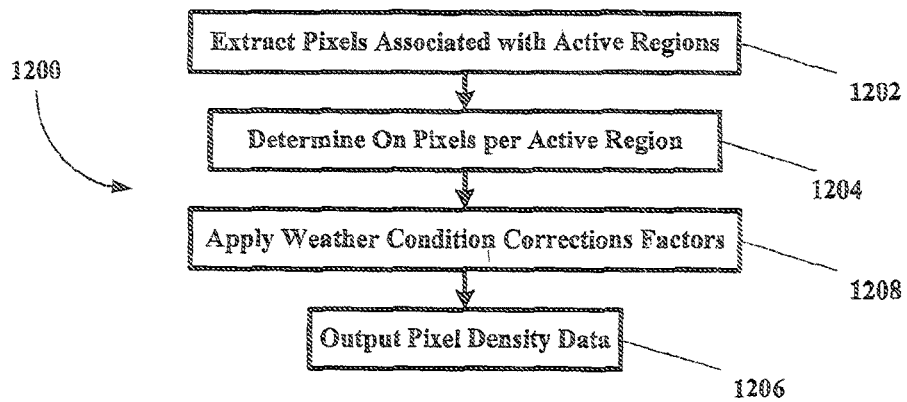
Figure 12C:
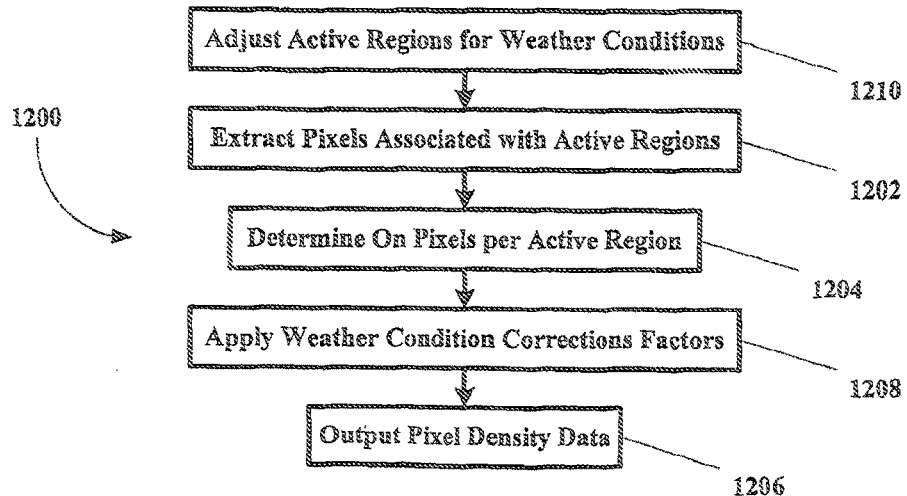

Referring now to FIGS. 12A-C, three preferred embodiments of a process active region subprocess are described, generally 1200, shown as a flow chart diagram. Looking at FIG. 12A, the subprocess starts with an extraction step 1202, where pixels associated with the active regions are extracted from the acquire image. Next, the "on" pixels are determined within the active regions, i.e., the pixels containing more than a background pixel intensity or more than a threshold pixel intensity, is a determination step 1204. The "on" pixel data are then used to output an active regions density data in an output step 1206. The resulting "on" pixel data is then used in the compute output values steps of FIGS. 9, 10 and 11. Of course, the pixel data derived from this process can relate to thermal data or compositional data depending on the light being collected and analyzed.

Looking at FIG. 12B, the subprocess starts with the extraction step 1202, where pixels associated with the active regions are extracted from the acquire image. Next, the "on" pixels are determined within the active regions, i.e., the pixels containing more than a background pixel intensity or more than a threshold pixel intensity, is a determination step 1204. Once the "on" pixels are identified, then weather condition correction factors are applied to the "on" pixel count in apply step 1208. These corrections are intended to correct the pixel data to compensate for weather conditions. The corrections factors can be determined by either data accumulated over time or from studies of acquired images under different weather conditions at constant plant output. The "on" pixel data are then used to output an active regions density data in an output step 1206. The resulting "on" pixel data is then used in the compute output values steps of FIGS. 9, 10 and 11. Of course, the pixel data derived from this process can relate to thermal data or compositional data depending on the light being collected and analyzed.

Looking at FIG. 12C, the subprocess starts with an adjust step 1210, where the active regions are corrected for weather conditions, such as a change in wind conditions, change in temperature, etc. After adjusting the active regions, control proceeds to the extraction step 1202, where pixels associated with the active regions are extracted from the acquire image. Next, the "on" pixels are determined within the active regions, i.e., the pixels containing more than a background pixel intensity or more than a threshold pixel intensity, is a determination step 1204. Once the "on" pixels are identified, then weather condition correction factors are applied to the "on" pixel count in apply step 1208. These corrections are intended to correct the pixel data to compensate for weather conditions. The corrections factors can be determined by either data accumulated over time or from studies of acquired images under different weather conditions at constant plant output. The "on" pixel data are then used to output an active regions density data in an output step 1206. The resulting "on" pixel data is then used in the compute output values steps of FIGS. 9, 10 and 11. Of course, the pixel data derived from this process can relate to thermal data or compositional data depending on the light being collected and analyzed.

Experimental Data Analysis

Figure 13:
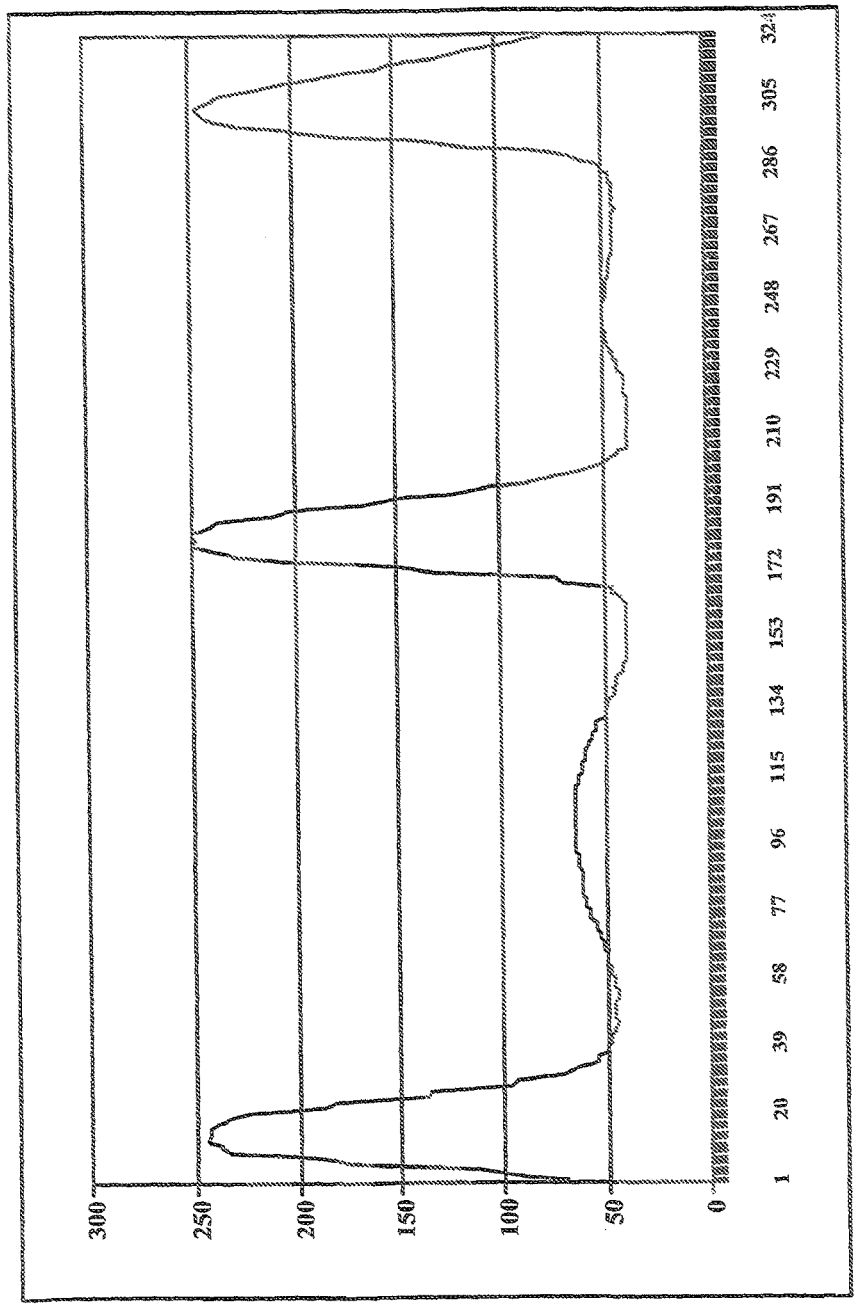
FIG. 13 depicts a plot of data collected form a three stack facility showing the thermal data image of the three stacks in the facility from an IR camera located approximately 1 km from the facility.

Referring now to FIG. 13, a plot of data collected form a three stack facility showing the thermal data image of the three stack in the facility from an IR camera located approximately 1 km from the facility.

Figure 14:
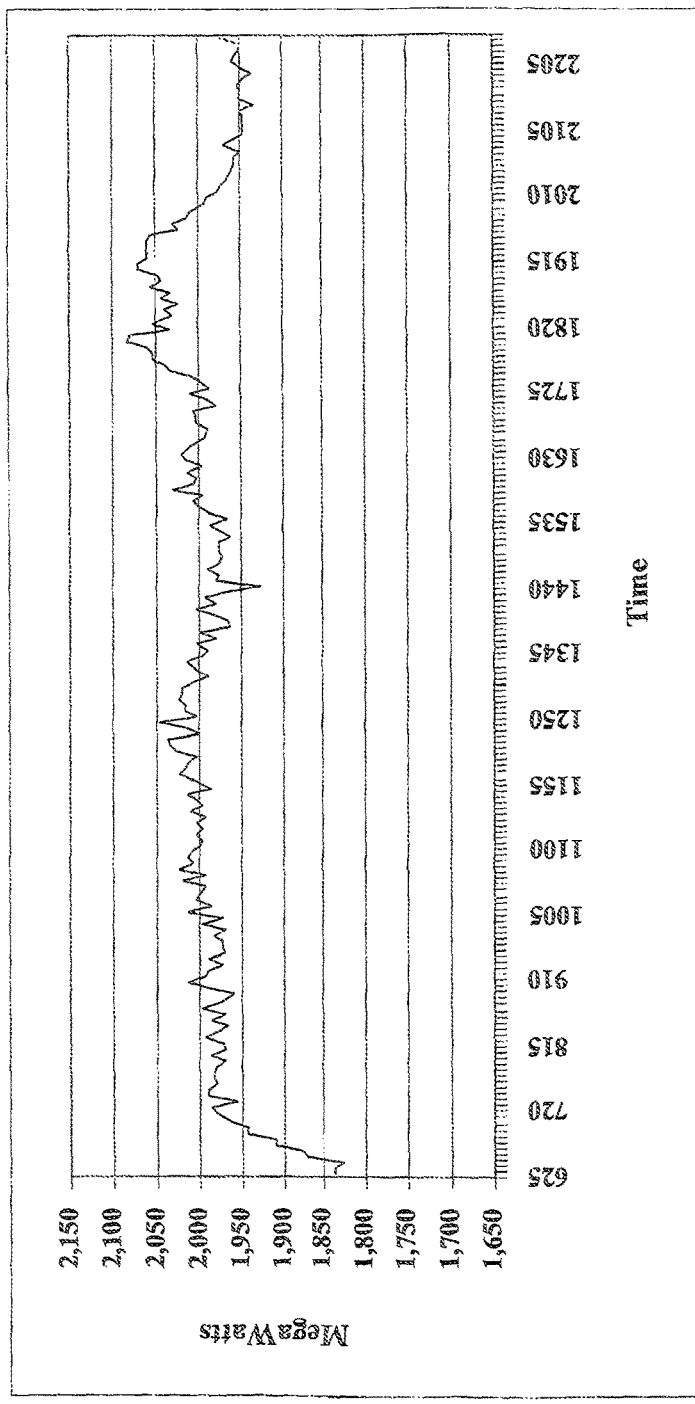
FIG. 14 depicts a plot of daily output activity for the facility in FIG. 13.

Referring now to FIG. 14, depicted is a plot of daily output activity for the facility in FIG. 13.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

The invention claimed is:

1. A method for monitoring, determining, and outputting at least one of plant output activity and capacity utilization of at least one power generating plant connected to a power grid comprising the steps of:

acquiring thermal images of at least one of one or more stack effluent plumes produced by the at least one power generating plant connected to the power grid using at least one thermal imaging camera, storing the acquired thermal images of the at least one of the one or more stack effluent plumes with at least one processing unit, transmitting the stored thermal images of the at least one of the one or more stack effluent plumes from the at least one processing unit to a central processing center having at least one processor, scanning the thermal images of the at least one of the one or more stack effluent plumes with the at least one processor to identify pixels within the thermal images containing more than at least one of a background pixel intensity and a threshold pixel intensity and thereby define active regions within the transmitted thermal images, associating pixel intensities within the active regions of the thermal images with the at least one of plant output activity and capacity utilization supplied by the at least one power generating plant to the power grid using the at least one processor, and transmitting from the central processing center to at least one of one or more user devices information concerning the at least one of plant output activity and capacity utilization supplied to the power grid based on the associated pixel intensities within the active regions of the thermal images.

2. The method of claim 1, further comprising the step of:
prior to the step of associating pixel intensities, correcting the pixel data to compensate for existing environmental factors using a data processing subsystem.

3. The method of claim 2, further comprising the steps of:
accumulating the information concerning the at least one of plant output activity and capacity utilization supplied to the power grid using an accumulation subsystem and
determining trends using a trend subsystem from the accumulated information concerning the at least one of plant output activity and capacity utilization supplied to the power grid.

4. The method of claim 3, further comprising the step of:
producing a report using a report subsystem evidencing the at least one of plant output activity and capacity utilization over time.

5. The method of claim 1, wherein the at least one of the one or more stack effluent plumes includes a plurality of stack effluent plumes, the at least one power generating plant includes a plurality of power generating plants, and the at least one thermal imaging camera includes a plurality of thermal imaging cameras, and wherein the step of acquiring thermal images includes acquiring thermal images of the plurality of the stack effluent plumes produced by the plurality of the power generating plants connected to the power grid using the plurality of thermal imaging cameras.

6. The method of claim 5, wherein the step of transmitting from the central processing center includes transmitting the information concerning the at least one of plant output activity and capacity utilization supplied to the power grid by each of the plurality of the power generating plants based on the associated pixel intensities within the active regions of the thermal images.

7. The method of claim 1, wherein the step of associating pixel intensities includes comparing the pixel intensities within the active regions of the thermal images against a baseline of previously acquired data, and further comprising a step of predicting disruptions in the power grid based on the comparison.

8. The method of claim 7, wherein the previously acquired data includes data from the stored thermal images collected over time.

9. The method of claim 7, wherein the step of transmitting from the central processing center includes transmitting information concerning the predicted disruptions from the central processing center to the at least one of the one or more user devices.

10. The method of claim 1, wherein the step of transmitting from the central processing center includes transmitting information concerning the at least one of plant output activity and capacity utilization of the at least one power generating plant to a clearinghouse where the information is accessible to a plurality of users in a form that reveals trends.

11. The method of claim 1, further comprising a step of connecting the at least one thermal imaging camera to the power grid using a power conditioning unit.

12. The method of claim 2, wherein the step of correcting includes correcting the pixel data to compensate for weather conditions using a data processing subsystem.

13. The method of claim 12, wherein the step of correcting includes applying a correction factor to pixels data in the active regions.

14. A method for monitoring, determining, and outputting at least one of plant output activity and capacity utilization of at least one power generating plant connected to a power grid comprising the steps of:

acquiring thermal images of at least one of one or more stack effluent plumes produced by the at least one power generating plant connected to the power grid using at least one thermal imaging camera, storing the acquired thermal images of the at least one of the one or more stack effluent plumes with at least one processing unit, transmitting the stored thermal images of the at least one of the one or more stack effluent plumes from the at least one processing unit to a processor, scanning the thermal images of the at least one of the one or more stack effluent plumes with the processor to identify pixels within the thermal images containing more than at least one of a background pixel intensity and a threshold pixel intensity and thereby define active regions within the transmitted thermal images, associating pixel intensities within the active regions of the thermal images with the at least one of plant output activity and capacity utilization supplied by the at least one power generating plant to the power grid using the processor, and transmitting from the processor to at least one of one or more user devices information concerning the at least one of plant output activity and capacity utilization supplied to the power grid based on the associated pixel intensities within the active regions of the thermal images.

* * * * *